United States Patent [19]

Nicolaou et al.

[11] Patent Number: 5,550,246

[45] Date of Patent: Aug. 27, 1996

[54] CALICHEAMICIN MIMICS

[75] Inventors: K. C. Nicolaou, La Jolla, Calif.; Emmanuel N. Pitsinos, Halandri, Greece

[73] Assignee: The Scripps Research Institute, La Jolla, Calif.

[21] Appl. No.: 301,968

[22] Filed: Sep. 7, 1994

[51] Int. Cl.[6] .................................................. C07D 213/04
[52] U.S. Cl. ............................. 546/300; 560/20; 560/107
[58] Field of Search ............................... 560/28, 20, 107; 546/293, 300

[56] References Cited

U.S. PATENT DOCUMENTS 5,264,586 11/1993 Nicolaou et al. ........................ 548/406

OTHER PUBLICATIONS

Nicolaou, et al., "Cell–Specific Regulation of Apoptosis by Designed Enediynes", *Proc. Natl. Acad. Sci*, 90: 3142–3146 (1993).

Nicolaou, et al., "Chemistry and Biology of Natural and Designed Enediynes", *Proc. Natl. Acad. Sci.*, 90: 5881–5888 (1993).

Nicolaou, et al., "Designed Enediynes: A New Class of DNA–Cleaving Molecules with Potent and Selective Anti Cancer Activity", *Science*, 256: 1172–1178 (1992).

Nicolaou, et al., "Total Synthesis of Calicheamicin", *J. Am. Chem. Soc.*, 114: 10082–10084 (1992).

Danishefsky, et al., "A Convergent Total Synthesis of Calicheamicin v", *Angew. Chem. Int. Ed.*, 33: 858–862 (1994).

Danishefsky, et al., "On the DNA Recognition Role of the Carbohydrate Sector in Calicheamicin: A Comparison of DNA Cleaving Capacity of Enantiomeric Calicheamicinones", *Angew. Chem. Int. Ed.*, 33: 855–857 (1994).

*Primary Examiner*—Joseph Conrad
*Attorney, Agent, or Firm*—Donald G. Lewis

[57] ABSTRACT

Synthetic calicheamicin mimics employ alternative activation triggers and trigger cites and include tithers for conjugation to DNA targeting systems.

3 Claims, 7 Drawing Sheets

| Cell type | 6 | 8 | Calicheamicin $\gamma_1^I$ | 7 | calicheamicin $\gamma_1^I$ | PM-9 |
|---|---|---|---|---|---|---|
| *Normal cell lines* | | | | | | |
| CHO | $1.1 \times 10^{-6}$ | $1.8 \times 10^{-7}$ | $1.2 \times 10^{-9}$ | $1.1 \times 10^{-5}$ | $4.3 \times 10^{-9}$ | $3.1 \times 10^{-6}$ |
| HMEC | $3.4 \times 10^{-7}$ | $1.1 \times 10^{-6}$ | $1.0 \times 10^{-9}$ | $2.4 \times 10^{-6}$ | $<10^{-12}$ | $6.3 \times 10^{-6}$ |
| NHDF | — | $9.8 \times 10^{-7}$ | $1.0 \times 10^{-9}$ | $2.9 \times 10^{-6}$ | $<10^{-12}$ | $5.0 \times 10^{-6}$ |
| RPMI766 | — | $3.1 \times 10^{-8}$ | $1.6 \times 10^{-9}$ | $2.5 \times 10^{-6}$ | $<10^{-12}$ | — |
| *Transformed cell lines* | | | | | | |
| BT-549 | $9.9 \times 10^{-7}$ | $5.3 \times 10^{-8}$ | $1.0 \times 10^{-9}$ | $4.5 \times 10^{-6}$ | $<10^{-12}$ | — |
| CAPAN1 | $1.2 \times 10^{-6}$ | $7.1 \times 10^{-7}$ | $1.3 \times 10^{-9}$ | $1.3 \times 10^{-5}$ | $<10^{-12}$ | $3.1 \times 10^{-9}$ |
| H322 | $1.7 \times 10^{-6}$ | $2.0 \times 10^{-6}$ | $1.7 \times 10^{-8}$ | $3.6 \times 10^{-5}$ | $1.0 \times 10^{-9}$ | $3.9 \times 10^{-7}$ |
| HL-60 | $2.0 \times 10^{-10}$ | $5.1 \times 10^{-10}$ | $<10^{-12}$ | — | $<10^{-12}$ | $3.6 \times 10^{-11}$ |
| HT-29 | $5.1 \times 10^{-6}$ | $3.6 \times 10^{-6}$ | $7.0 \times 10^{-9}$ | $1.2 \times 10^{-5}$ | $<10^{-12}$ | $1.6 \times 10^{-6}$ |
| M24-MET | $4.1 \times 10^{-7}$ | — | $1.0 \times 10^{-9}$ | — | $<10^{-12}$ | — |
| MCF-7 | $2.6 \times 10^{-6}$ | $1.9 \times 10^{-6}$ | $4.1 \times 10^{-8}$ | $3.6 \times 10^{-6}$ | $1.2 \times 10^{-11}$ | $7.8 \times 10^{-7}$ |
| MOLT-4 | $4.4 \times 10^{-11}$ | $1.3 \times 10^{-12}$ | $<10^{-12}$ | $1.9 \times 10^{-7}$ | $<10^{-12}$ | $<10^{-12}$ |
| OVCAR-3 | $4.8 \times 10^{-6}$ | $1.3 \times 10^{-6}$ | $2.2 \times 10^{-9}$ | $1.7 \times 10^{-5}$ | $<10^{-12}$ | $7.8 \times 10^{-7}$ |
| UCLA-P-3 | $4.2 \times 10^{-6}$ | $1.8 \times 10^{-6}$ | $1.7 \times 10^{-9}$ | $1.3 \times 10^{-5}$ | $<10^{-12}$ | $9.8 \times 10^{-8}$ |
| PC-3 | $3.4 \times 10^{-8}$ | $6.3 \times 10^{-7}$ | $4.4 \times 10^{-9}$ | $7.5 \times 10^{-6}$ | $<10^{-12}$ | — |
| SIHA | $5.0 \times 10^{-7}$ | $1.6 \times 10^{-6}$ | $6.7 \times 10^{-10}$ | $1.4 \times 10^{-6}$ | $<10^{-12}$ | — |
| SK-MEL 28 | $1.8 \times 10^{-6}$ | $2.4 \times 10^{-6}$ | $1.6 \times 10^{-9}$ | $5.1 \times 10^{-5}$ | $<10^{-12}$ | — |
| U251 | $1.3 \times 10^{-6}$ | $7.4 \times 10^{-8}$ | $1.1 \times 10^{-9}$ | $4.1 \times 10^{-5}$ | $9.9 \times 10^{-9}$ | — |
| 786-0 | $1.4 \times 10^{-5}$ | $3.7 \times 10^{-7}$ | $1.0 \times 10^{-8}$ | $1.8 \times 10^{-5}$ | $<10^{-12}$ | — |
| L1210 | $2.7 \times 10^{-8}$ | — | — | — | — | $1.3 \times 10^{-9}$ |
| SK-N-SH | $7.8 \times 10^{-9}$ | — | — | — | — | — |

FIG. 8

CALICHEAMICIN MIMICS

GOVERNMENT RIGHTS

This invention was made, in part, with government support under Grant No. NIH CA46446. The U.S. government may have certain rights in the invention.

SPECIFICATION

1. Field of Invention

The invention relates to a synthetic calicheamicin mimics having designed initiation mechanisms while retaining DNA cleavage activity, cytotoxicity, and apoptosis activity.

2. Background

Calicheamicin $\gamma_1^I$ is a bacterial derived natural product known to have activity as an antitumor antibiotic. Calicheamicin $\gamma_1^I$ is a member of a class of enediyne antitumor antibiotics which share a common mode of action. The total synthesis of calicheamicin $\gamma_1^I$ has been achieved by two groups, viz. K. C. Nicolaou et al. (*Journal of the American Chemical Society* (1992):vol. 114, pp 10082–10084) and S. J. Danishefsky et al. (*Angew. Chem. Int. Ed. Engl.* (1994):vol. 33, pp 858–862). Antibody conjugates of calicheamicin $\gamma_1^I$ are currently in clinical trials for potential use in chemotherapy. (L. M. Hinman et al., *Cancer Res.* (1993):vol. 53, pp 3336–3342.)

Figure 1:
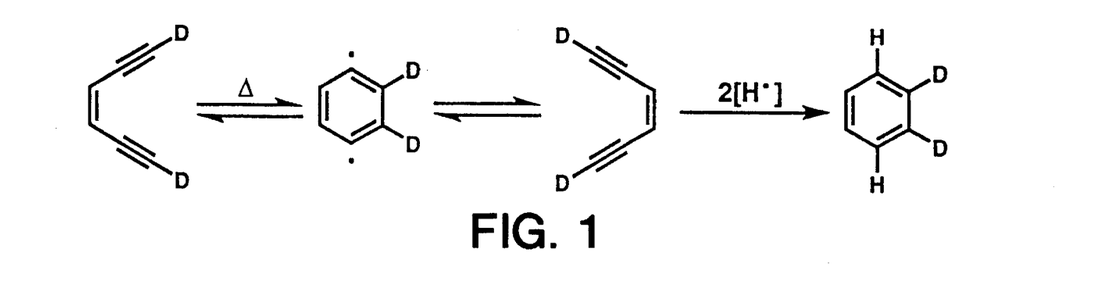

The structure of calicheamicin $\gamma_1^I$ was first established in 1987 by M. D. Lee et al. at Lederle laboratories. (*Journal of the American Chemical Society* (1987):vol. 109, pp 3466–3468.) Subsequently, calicheamicin $\gamma_1^I$ (FIG. 1A) was reported by K. C. Nicolaou et al to be the most potent naturally occurring member of the enediyne class of antitumor antibiotics (*Angew. Chem. Int. Ed. Engl.* (1991):vol. 30, pp 1387–1530).

The growing number of these antibiotics has been paralleled by an increasing interest in them from members of the chemical, biological and medical communities. Advances in synthetic efforts, culminating in total syntheses of calicheamicin $\gamma_1^I$ and a number of designed analogs (K. C. Nicolaou et al., *Proc. Natl. Acad. Sci. USA* (1993):vol. 90, pp 5881–5888) have been entwined with advances in research related to their mechanism of action. M. D. Lee et al. characterized the chemical interaction of calicheamicins with DNA. (*Acc. Chem. Res.* (1991):vol. 24, pp 235–243.) More particularly, P. C. Dedon et al. disclosed that calicheamicin employs a free-radical mechanism to achieve sequence-dependent bistranded DNA lesions (*Chem. Res. Toxicol.* (1992):vol. 5, pp 311–332). Furthermore, Uesugi et al. disclosed that calicheamicin $\gamma_1^I$ employs a sequence recognition process with DNA and "induced fit" mechanism to achieve its selectivity (*Biochemistry* (1993):vol. 32, pp 4622–4627.

Figure 2:
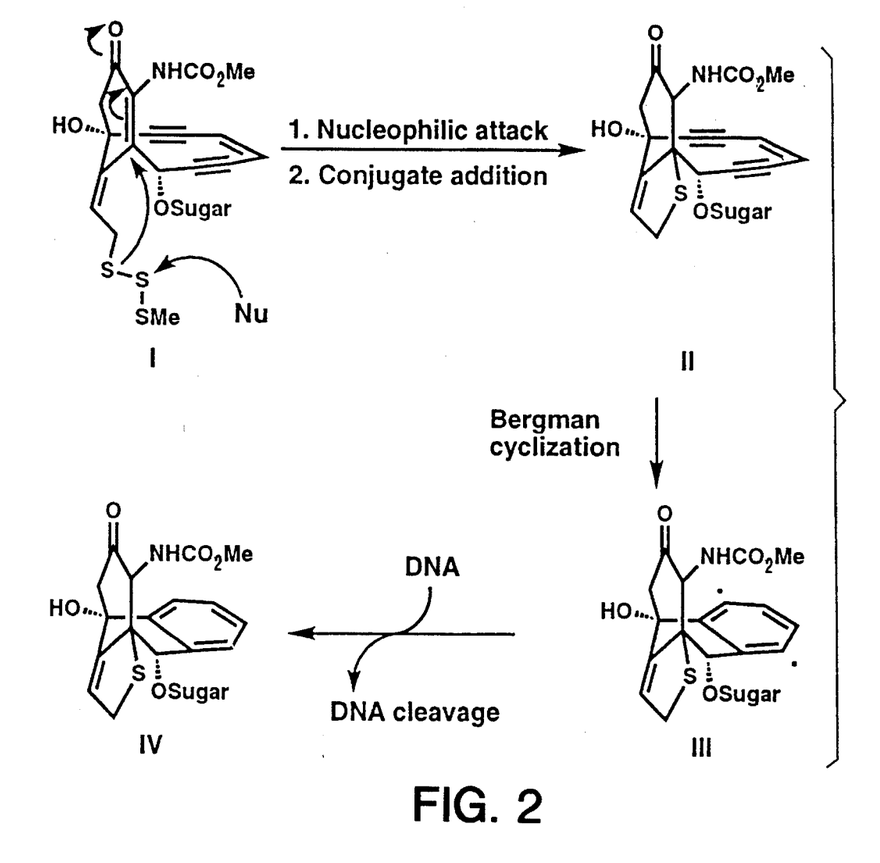

The molecular architecture of calicheamicin $\gamma_1^I$ exemplifies the efficiency of design common to the enediyne class of antitumor antibiotics. The structure can be viewed as consisting of three functional domains with distinct roles:

(a) the novel oligosaccharide chain, which allows the sequence selective binding of the drug in the minor groove of double-stranded DNA (Dedon, supra);

(b) the enediyne moiety (represented by calicheamicinone), which is capable of undergoing a Bergman cycloaromatization (FIG. 2), generating benzenoid diradicals that can cleave double-stranded DNA via hydrogen atom abstraction (R. G. Bergman, *Acc. Chem. Res.* (1973):vol. 6, pp 25–31); and

Figure 3:
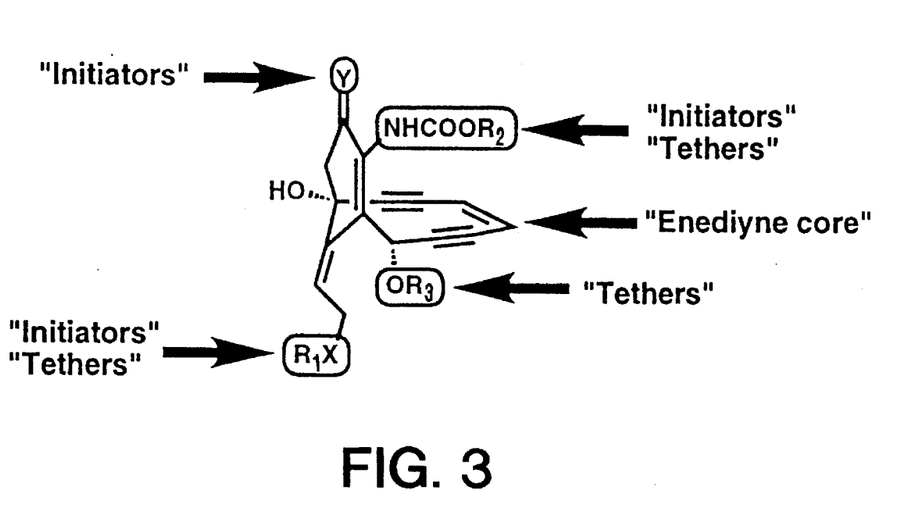

(c) the trisulfide group, which serves as a triggering device to initiate the cascade of reactions that leads to DNA damage (FIG. 3) (A. G. Myers et al., *Journal of the American Chemical Society* (1994):vol. 116, pp 1255–1271).

calicheamicin $\gamma_1^I$

Other members of the class of enediyne antitumor antibiotics include esperamicin $A_1$, neocarzinostatin chromophore, dynemicin A, kedarcidin chromophore, and C-1027 chromophore. The structure of esperamicin $A_1$ was established by J. Golik et al. at Bristol Meyers Squibb. (*Journal of the American Chemical Society* (1987):vol. 109, pp 3462–3464.) The previously known neocarzinostatin chromophore was included within the class when it was disclosed by I. H. Goldberg to have a mode of action similar to calicheamicin $\gamma_1^I$ and esperamicin $A_1$. (*Acc. Chem. Res.* (1991):vol. 24, pp 191–198.) The group continued to expand with the discoveries of dynemicin A (M. Konishi et al., *J. Antibiot.* (1989):vol. 42, pp 1449–1452), kedarcidin chromophore (J. E. Leet et al. *Journal of the American Chemical Society* (1992):vol. 114, 7946–7948) and C-1027 chromophore (K. Yoshida et al., *Tetrahedron Lett.* (1993):vol. 34, 2637–2640).

The DNA-cleaving activity and anticancer activity of natural enediynes have been partially reproduced by various designed enediynes (K. C. Nicolaou et al., *Science* (1992):vol. 256, pp 1172–1178.) More particularly, calicheamicin $\Theta_1^I$, a rationally designed and totally synthetic enediyne, has been demonstrated to have extremely potent and selective DNA cleaving properties and apoptosis inducing activity. (K. C. Nicolaou et al., *Angew. Chem. Int. Ed. Engl.* (1993):vol 33, pp 183–186 Calicheamicin $\Theta_1^I$ is structurally identical to calicheamicin $\gamma_1^I$ except for the substituent at the allylic position of the exocyclic chain.

calicheamicin theta $_1{}^I$

What is needed are simple synthetic biological mimics of calicheamicin $\gamma_1{}^I$ having enhanced or altered biological activity with minimal molecular complexity.

SUMMARY

Simple biological mimics of calicheamicin and chemical intermediates employed in the synthesis of such mimics are disclosed. Each of the disclosed mimics of calicheamicin includes the following elements:

1. An enediyne core ring structure identical to the enediyne core ring structure of calicheamicin;
2. One or more novel initiators for triggering a Bergman cycloaromatization of the enediyne core ring structure and the formation or a diradical; and
3. One or more tethers to which substituents may be conjugated for binding the mimic to a DNA targeting delivery system.

Several different initiators and initiator cites are disclosed. Each initiator and initiator cite is characterized by the conditions under which it triggers the cycloaromatization of the enediyne core ring structure to form a benzenoid diradical. Naturally occurring calicheamicin $\gamma_1^I$ employs a trisulfide trigger cited at the allylic position of the exocyclic chain. It is disclosed herein that initiators may be introduced at any of three points on the enediyne core ring structure, viz.:

1. The allylic position of the exocyclic chain;
2. The enone carbonyl; and
3. The urethane moiety.

Several different tethers and tithering cites are also disclosed. Naturally occurring calicheamicin $\gamma_1^I$ is tethered to an oligosaccharide DNA binding domain at the secondary propargylic hydroxyl group via a glycosidic bond. It is disclosed herein that DNA binding domains may be introduced at any of three points on the enediyne ring, viz.:

1. The allylic position of the exocyclic chain;
2. The secondary propargylic hydroxyl group; and
3. The urethane moiety.

The disclosed mimics of calicheamicin were characterized and shown to exhibit significant cytotoxicity and DNA cleaving properties. However, when compared to the biological profiles of calicheamicins $\gamma_1^I$ and $\Theta_1^I$, the calicheamicin mimics disclosed herein were found to be less potent. In contrast to the highly potent calicheamicins $\gamma_1^I$ (naturally occurring) and $\Theta_1^I$ (synthetic), the designed mimics disclosed herein cause primarily single strand DNA cuts and are weaker inducers of apoptosis. This reflects their relatively weaker affinities to DNA and lack of specific positioning along the minor groove. These attenuated biological properties are due to the lack of the DNA binding domain for positioning the enediyne moiety adjacent to the DNA so as to make double strand DNA cleavage a favorable and efficient process. The ability of the enediynes to cause double strand cuts to DNA is correlated with their ability to induce apoptosis.

Compounds 3, 4, and 10 are suitable for conjugation to delivery systems such as antibodies and other proteins, oligonucleotides, oligosaccharides, DNA intercalators or groove binders which target the disclosed calicheamicin mimics to DNA. When these calicheamicin mimics are attached to a targeting delivery system, their ability to cleave double strands of DNA can be enhanced. In turn, this enhanced nuclease acitivy can lead to enhanced apoptosis activity. Accordingly, compounds 3, 4, and 10 can serve as "molecular warheads" for inducing apoptosis when attached to a DNA targeting delivery system.

The disulfide 9 and the p-nitrobenzoate 6 (Scheme 1) exhibited potent DNA-cleaving and cytotoxic activities and apoptosis-inducing properties and were amongst the most biologically active of the synthesized mimics.

BRIEF DESCRIPTION OF THE DRAWINGS

FIG. 1 illustrate the Bergman cycloaromatization reaction for an enediyne.

FIG. 2 illustrates the cascade of events which triggers the cycloaromatization of calicheamicin $\gamma_1^I$ and subsequent cleave of DNA.

FIG. 3 illustrates the design of calicheamicin $\gamma_1^I$ mimics.

FIG. 4A illustrates the cascade of events which triggers the cycloaromatization of Type I and Type II mimics. X=O, NH, or S.

FIG. 4A illustrates the cascade of events which triggers the cycloaromatization of Type III mimics. Y=$OCH_2CH_2O$ or O.

FIG. 5 illustrates the synthesis of Type I and Type II mimics.

FIG. 6 illustrates the synthesis of Type II and Type III mimics.

FIG. 7 illustrates a comparison of cytotoxicities of designed enekiynes 1–4, 6–15, and 35 against transformed and normal cells.

FIG. 8 illustrates a comparison of cytotoxicities of designed enediynes 6–8, calicheamicin $\gamma_1^I$, calicheamicin $\Theta_1^I$, and PM-9 against a panel of 17 transformed cell lines and 4 normal cell lines.

DETAILED DESCRIPTION

Molecular design:

FIG. 3 summarizes a number of possible structural modifications on the calicheamicinone core that were considered. Organic chemistry principles were used in guiding the design of potentially active compounds which were required to fulfill the following general criteria:(a) be chemically stable under neutral conditions but capable to undergo the Bergman cycloaromatization reaction upon suitable activation; (b) be structurally simple to allow easy access by chemical synthesis; (c) allow for tethering to suitable delivery systems and other desirable moieties through appropriate functionalities; and (d) be equipped with suitable initiators that may be activated under mild chemical or biological conditions.

Figure 4A:
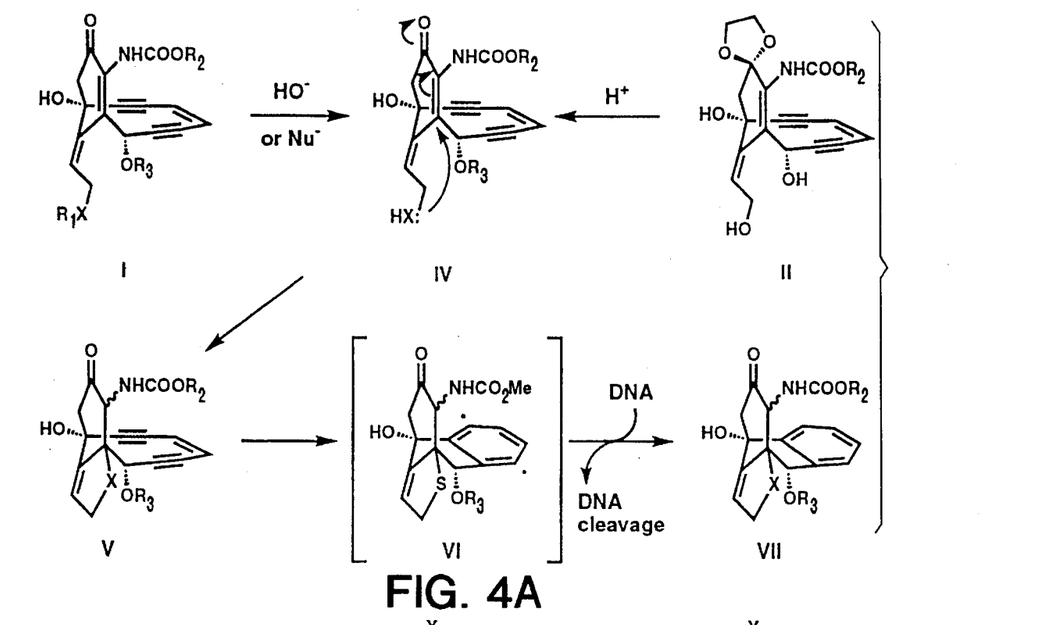
Figure 4B:
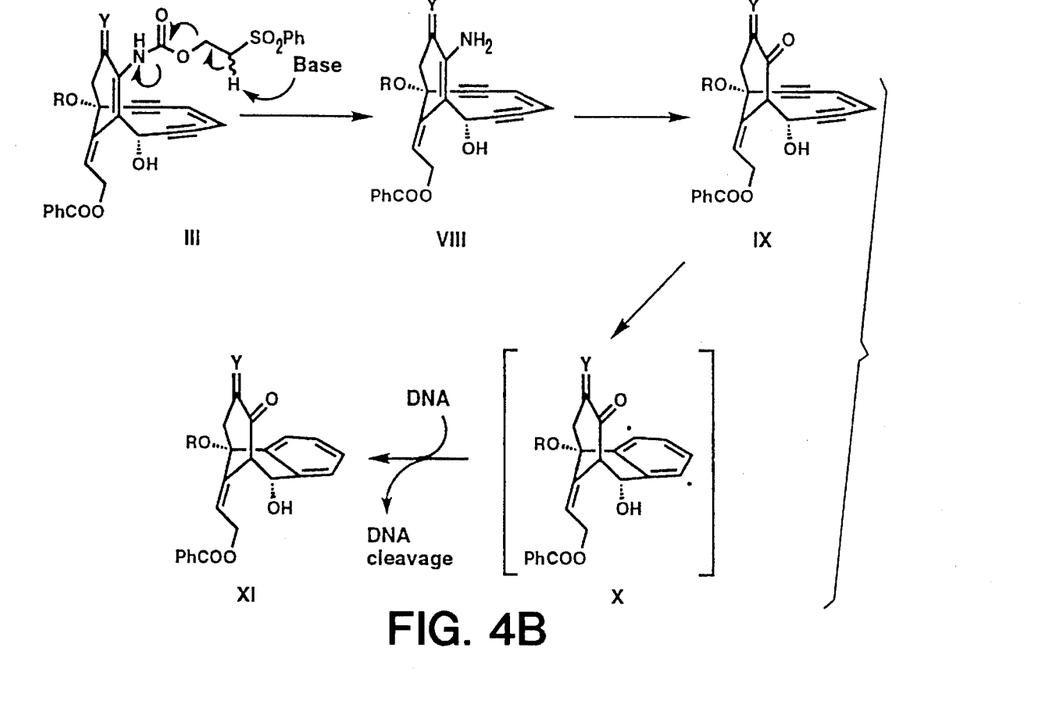

Following Nature's mechanism of activation of calicheamicin $\gamma_1^I$ (FIG. 2), we envisioned a number of variants (structure I, FIG. 4A) utilizing the generation of oxygen-, nitrogen- or sulfur-centered nucleophiles as a means of activation towards the Bergman reaction. J. N. Haseltine et al. discloses earlier experimental modeling of the priming mechanism of the calicheamicin antibiotics wherein activation is achieved by the addition of intramolecular nucleophiles to the bridgehead double bond. (*J. Am. Chem. Soc.* (1989):vol. 111, pp 7638–7640 and *J. Am. Chem. Soc.* vol. 113, pp 3850–3866.) An interesting alternative (structure II, FIG. 4A) in which the carbonyl group of the enone system was protected as a ketal, was considered as a compound capable of activation under acidic conditions employed by Haseltine above. Diverging from the above mode of activation and relying on the known propensity of enamines to hydrolyze to carbonyl compounds, we designed compound III (FIG. 4B), which was envisioned to undergo activation as shown in FIG. 4B.

Inspired by Nature's molecular design, as witnessed in calicheamicin, we chose the secondary propargylic alcohol as an appropriate handle for attachment of tethers. Therefore, compounds 3 and 4 (FIG. 5) were targeted for synthesis. The capability to have a thiol group at the allylic position, and the utilization of such functionalities in the synthesis of immunoconjugates prompted the design of mimics suitably activated for the construction of non-symmetric disulfides at this position. (L. M. Hinman et al. *Cancer Res.* (1993):vol. 53, 3336–3342.) Such groups could play a dual role as reductively cleavable initiators and tethering devices.

Chemical Synthesis.

Figure 5:
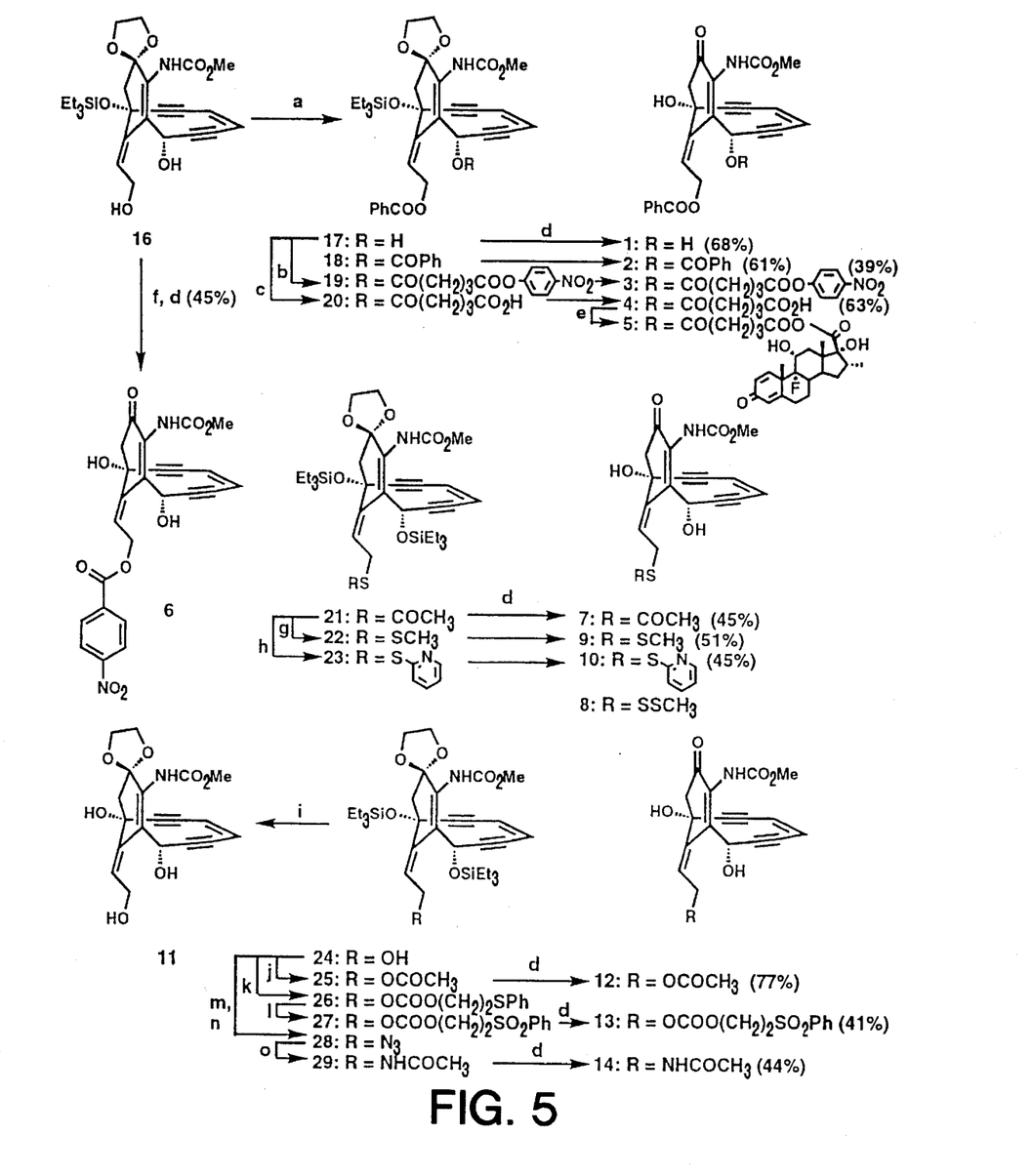
Figure 6:
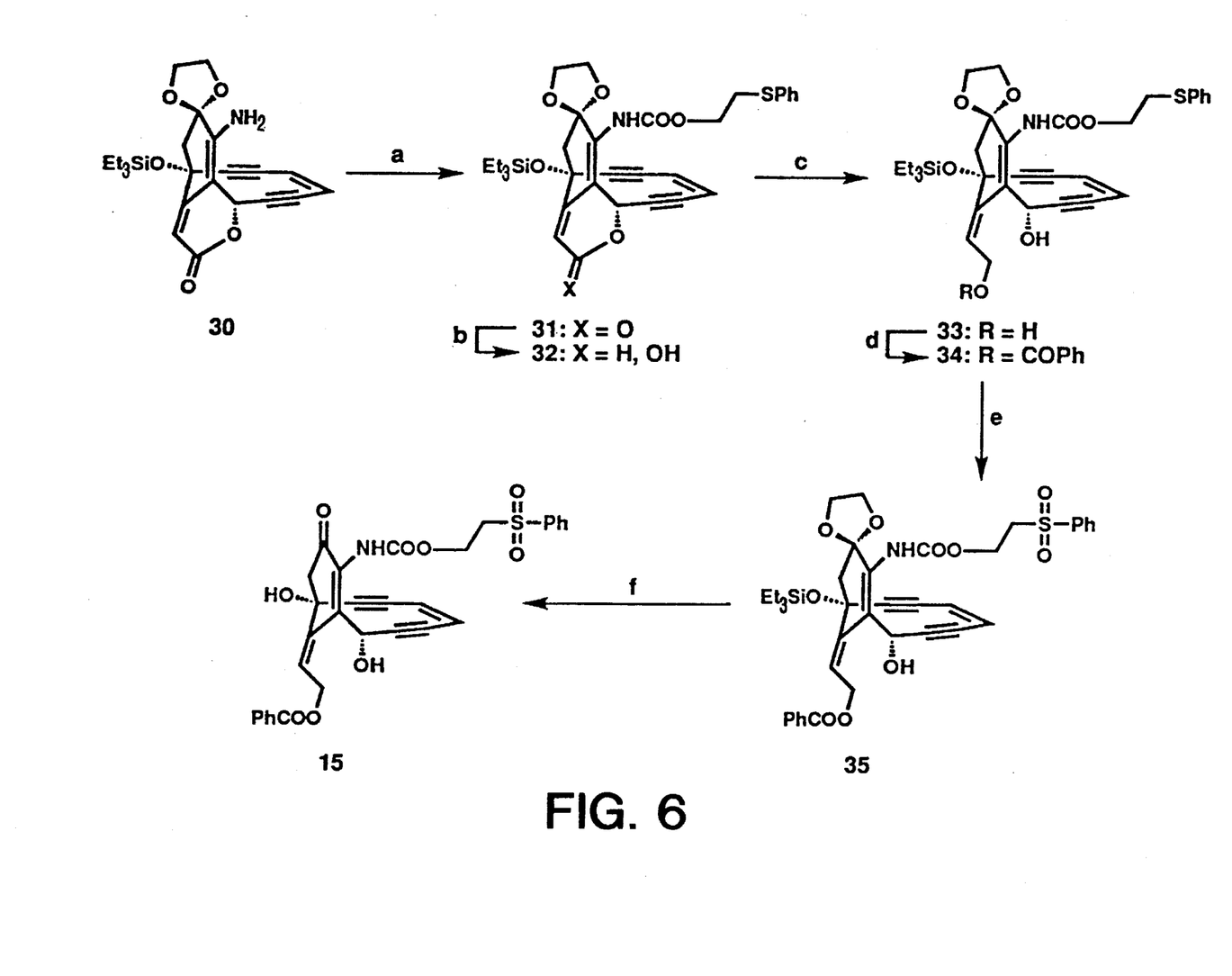

FIGS. 5 and 6 summarize the chemical synthesis of the targeted compounds (1–7, 9–15). For their synthesis, advantage was taken of our previously developed route to calicheamicinone (8) which delivers the advanced intermediate 16 (FIG. 5) in optically active form, as disclosed by A. L. Smith et al., *J. Am. Chem. Soc.* (1992):vol. 114, pp 3134–3136. Thus, selective benzoylation of this diol afforded monobenzoate 17 as the major product accompanied by the corresponding dibenzoate 18. Concomitant removal of both the ketal and silyl protecting groups from 17 and 18 by aqueous acid treatment resulted in the formation of compounds 1 and 2, respectively. p-Nitrobenzoate 6 (FIG. 5) was synthesized in a similar fashion from 16.

The differentiation of the functional groups in 17 allowed the introduction of a tethering group at the propargylic position using glutaric anhydride under basic conditions to afford 20 and 19 (after coupling with p-nitrophenol). These compounds were converted to enones 3 and 4, respectively, under acidic conditions. In order to probe the biological effect of damaging a steroid receptor involved in gens regulation, desoxymethasone was conjugated with 4 to afford compound 5 according to the method of K. R. Yamamoto in *Molecular development Biology; Expressing foreign genes*, 43rd Symposium of Society for developmental biology, (Bagorad, L. & Adelman, G., eds.), pp. 131–148, Alan Liss, New York.

Following another vein, the readily available thioacetate 21 (see Smith, supra) was converted to the free thiol with diisobutylaluminum hydride (DIBAL) or sodium methoxide, which was reacted in situ with MeSSCOOMe, according to the method of S. J. Brois et al. (*J. Am. Chem. Soc.* (1970):vol. 92, pp 7629–7631) or 2,2'-dipyridyl disulfide (aldrithiol-2), according to the method of J. Carlsson et al. (*Biochem. J.* (1978); vol. 73, pp 723–737) to afford the methyl disulfide 22 or the 2-pyridyl disulfide 23, respectively. Deprotection of these intermediates (21–23) as above furnished the expected enones 7, 9, and 10, respectively (FIG. 5). Another report on compound 7 is provided by J. Aiyor et al. in *Angew. Chem. Int. Ed. Engl.* (1994):vol. 33, pp 855–858.

Compound 24, another readily available intermediate from the calicheamicin synthesis (K. R. Yamamoto, supra) was utilized as a branching point for the synthesis of a new series of designed calicheamicinones (11–14, FIG. 5). Thus, desilylation of 24 led to compound 11, whereas acetylation furnished compound 25. Esterification with the appropriate chloroformate allowed the formation of carbonmate 26, which was oxidized smoothly to afford the sulfone derivative 27. On the other hand mesylation of alcohol 24 followed by azide displacement afforded azide 28, which was reduced and acetylated in situ, according to the method of T. Rosen, *J. Org. Chem.* (1988):vol. 53, pp 1580–1582, leading to acetamide 29. Deketalization of 25, 27, and 29 gave enones 12, 13, and 14, respectively (FIG. 5).

The synthesis of compound 15, containing the 2'-phenylsulfonylethyl carbonate group on the nitrogen as an activator, proceeded as outlined in FIG. 6. The readily available amine 30 (A. L. Smith, supra) was converted to urethane 31 in 82% yield, by treatment with oxalyl chloride and 2-phenylthioethanol in the presence of pyridine. Lactone 31 was then reduced sequentially with diisobutylaluminum hydride (DIBAL) and NaB$_4$ leading to diol 33 via lactol 32 (63% overall yield). Selective monobenzylation of the primary alcohol in diol 33 furnished monobenzoate 34 (69%), which was oxidized by 1,3-dicyclohexylcarbodiimide (m-CPBA) to sulfone 35 in 100% yield. Finally, deprotection under aqueous acid conditions generated the targeted enediyne 15 in 36% yield.

The reaction conditions indicated in FIG. 5 are summarized as follows:

Reagents and conditions for reaction "a":2.6 equivalents of PhCOCl and 6.0 equivalents of pyridine in CH$_2$Cl$_2$ for 1.5 hours at −15° C., yielding 68% of 17 and 26% of 18.

Reagents and conditions for reaction "b":9.0 equivalents of glutaric anhydride and 12.0 equivalents of 4-dimethylaminopyridine in CH$_2$Cl$_2$ for 2.5 hours at 25° C.; then 9.0 equivalents of 1,3-dicyclohexylcarbodiimide and 9.0 equivalents of p-nitrophenol for 2.0 hour, yielding 46%.

Reagents and conditions for reaction "c":1.6 equivalents of 4-dimethylaminopyridine and 3.0 equivalents of glutaric anhydride for 6 hours at 25° C., yielding 69%.

Reagents and conditions for reaction "d":5.5 equivalents of TsOH-H$_2$O in aqueous THF at 25° C.

Reagents and conditions for reaction "e":2.4 equivalents of desoxamethasone, 1.5 equivalents of 1,3-dicyclohexylcarbodiimide, and 0.5 equivalents of 4-dimethylaminopyridine in CH$_2$Cl$_2$ for 2.0 hour at 25° C. yielding 53%.

Reagents and conditions for reaction "f":3.0 equivalents of pyridine, 05 equivalents of 4-dimethylaminopyridine, and 2.3 equivalents of equivalens of p-nitrobenzoylchloride in CH$_2$Cl$_2$ for 1.5 hour at −15° C., yielding 66%.

Reagents and conditions for reaction "g":7.0 equivalents of diisobutylaluminum hydride in CH$_2$Cl$_2$ for 30 minutes at −78° C.; then 10.0 equivalents of MeOH, while reducing the temperature from −78° C. to 25° C. and adding 4.2 equvalents of MeSSCOOMe for 12 hours, yielding 70%.

Reagents and conditions for reaction "h":4.3 equivalents of NaOMe in MeOH for 3 hours at 0° C.; then 5.0 equivalents of aldrthiol-2 for 3 hours, yielding 66%.

Reagents and conditions for reaction "i":HF-Pyridine in THF at 0° C. to 25° C. over 4 hours, yielding 96%.

Reagents and conditions for reaction "j":4.0 equivalents of pyridine, 0.5 equivalents of 4-dimethylaminopyridine, and 3.0 equivalents of Ac$_2$O at 0° C. for 2 hours, yielding 92%.

Reagents and conditions for reaction "k":7 equivalents of 4-dimethylaminopyridine and 20.0 equivalents of PhSCH$_2$CH$_2$OCOCl in CH$_2$Cl$_2$ at 0° C. fopr 4 hours, yielding 88%.

Reagents and conditions for reaction "l":4.0 equivalents of m-CPABA in CH$_2$Cl$_2$ at 25° C. for 2 hours, yielding 94%.

Reagents and conditions for reaction "m":10.0 equivalents of pyridine, 5.0 equivalents of MsCl, and 0.5 equivalents of 4-dimethylaminopyridine in CH$_2$Cl$_2$ at 0° C. for 3 hours.

Reagents and conditions for reaction "n":10.0 equivalents of NaN$_3$ in DMF at 50° C. yielding 53%.

Reagents and conditions for reaction "o":AcSH at 25° C. for 2 hours, yielding 48%.

The reaction conditions indicated in FIG. 6 are summarized as follows:

Reagents and conditions for reaction "a":10.0 equivalents of pyridine, 3.0 equivalents of (COCl)$_2$ in CH$_2$Cl$_2$ at 25° C. for 30 minutes; then 10.0 equivalents of pyridine and 10.0 equivalents of PhSCH$_2$CH$_2$OCOCl for 2.0 hours, yielding 82%.

Reagents and conditions for reaction "b":2.2 equivalents of diisobutylaluminum hydride in CH$_2$Cl$_2$ at −78° C. for 30 minutes, yielding a 4:1 mixture of epimers, 95%.

Reagents and conditions for reaction "c":55.0 equivalents of NaBH$_4$ in MeOH at 0° C. for 2 hours, yielding 66%.

Reagents and conditions for reaction "d":5.0 equivalents of pyridine and 2.4 equivalents of PhCOCl at 0° C. for 1 hour, yielding 60%.

Reagents and conditions for reaction "e":5.0 equivalents of m- 1,3-dicyclohexylcarbodiimide in CH$_2$Cl$_2$ at 25° C. for 1.5 hour, yielding 100%.

Reagents and conditions for reaction "f":5.5 equivalents of TSOH-H$_2$O in aqueous THF at 25° C. for 24 hour, yielding 36%.

DNA Cleaving Activity.

The synthesized compounds were tested for their ability to cleave DNA under a variety of conditions. Supercoiled DNA (X174 or pBR322) was incubated with each compound in buffer solutions at different pH values and in the presence or absence of 2-mercaptoethanol. DNA damage was assayed by agarose gel electrophoresis. Compounds 6, 7–9, and 13 (data not shown) exhibited the highest potencies in the DNA cleavage assay. With the exception of compounds 8 and 9, in all cases cleavage was observed under basic conditions. DNA damage to some extent was observed at neutral and slightly acidic media. This effect maybe due to local DNA basicity or nucleophilicity as speculated earlier for a series of dynemicin A mimics.

The following observations merit special comment. The most significant observation in these DNA cleaving studies is the predominance of single DNA strand breaks for the aglycones in contrast to the double strand breaks caused by the natural calicheamicins, according to the method of J. Aiyor, supra. The dibenzoylated derivative 2 exhibits lower potency in DNA cleavage as compared to 1. This suggests a possible role of the propargylic hydroxyl in the hydrolysis of the allylic benzoate (an effect previously observed by J. N. Haseltine (supra), the event that leads to the Bergman activation cascade. The relative efficiencies of compounds 1, 2, 6, 7, and 12 in cleaving DNA correlate well with molecular structure and reflect the expectations of the molecular design. Thus the more labile p-nitrobenzoate 6 damages supercoiled DNA to a greater extent than benzoate 1 or acetate 12 under the same conditions. This compound also cleaves DNA with progressively higher efficiency at increasing pH values, as expected from higher rates of hydrolysis which leads to activation. Disulfide 9 exhibits its DNA cleaving activity in the presence of added thiol, as expected from its propensity to cleave under the influence of the thiol nucleophile. Finally, given the lability of the 2'-phenylsulfone ethyl carbamate moiety under basic conditions (K. C. Nicolaou et al., *Science* (1992), vol. 256, pp 1172–1178), the failure of compound 35 (FIG. 6) to cleave DNA at a range of pH values (pH 6–8.5) can only be attributed to a relatively high and unexpected stability of either the postulated enamine intermediate VIII or ketone IX (Y=OCH$_2$CH$_2$O, FIG. 4B). Similar observations were reported by M. F. Semmelhack et al. in *J. Am. Chem. Soc.* vol. 115, pp 11618–11619.. The DNA cleaving activity of 15 may be due to activation via benzoate hydrolysis rather than enamine-induced triggering.

DNA cleaving activity of various compounds were measured as follows:

Panel A:ΦX174 DNA (100 micro molar per base pair) was incubated for 2.5 hours at 37° C. with coumpound 6 in various buffer solutions (5 mM) and analyzed by electrophoresis (1% agarose gel, ethidium bromide stain). Lanes 1–4:DNA controls at pH 6.0, 7.0, 7.5, adn 8.5 respectively. Lanes 5–8:compound 6 (1 mM) at pH 6.0, 7.0, 7.5, and 8.5 respectively.

Panel B:ΦX174 DNA (100 micro molar per base pair) was incubated for 8 hours at 37° C. with compounds 1, 2, 6, 7, 12, and 15 in buffer solutions (5 mMm tris-HCl, pH 8.5) and analyzed by electrophoresis (1% agarose gel, ethidium bromide stain). Lane 1:supercoiled ΦX174 DNA control; Lane 2:1 (5 mM); Lane 3:6 (5 mM); Lane 4:2 (10 mM); Lane 5:12 (5 mM); lane 6:7 (5 mM); Lane 7:15 (10 mM); Lanes 8:nicked ΦX174 DNA standard.

Cytotoxicity.

Cytotoxicity studies with the synthesized compounds were carried out using a broad spectrum of cell lines, ranging from the drug resistant SK-Mel-28 melanoma to the highly sensitive Molt-4 leukemia cells, to assess antineoplastic activity and cell-type selectivity. A number of these compounds (e.g. 6 and 9) exhibited high cytotoxicities, with the most potent ones being comparable to calicheamicinone (8) but considerably less potent than calicheamicin $\gamma_1^I$ (Table 1).

Figure 7:
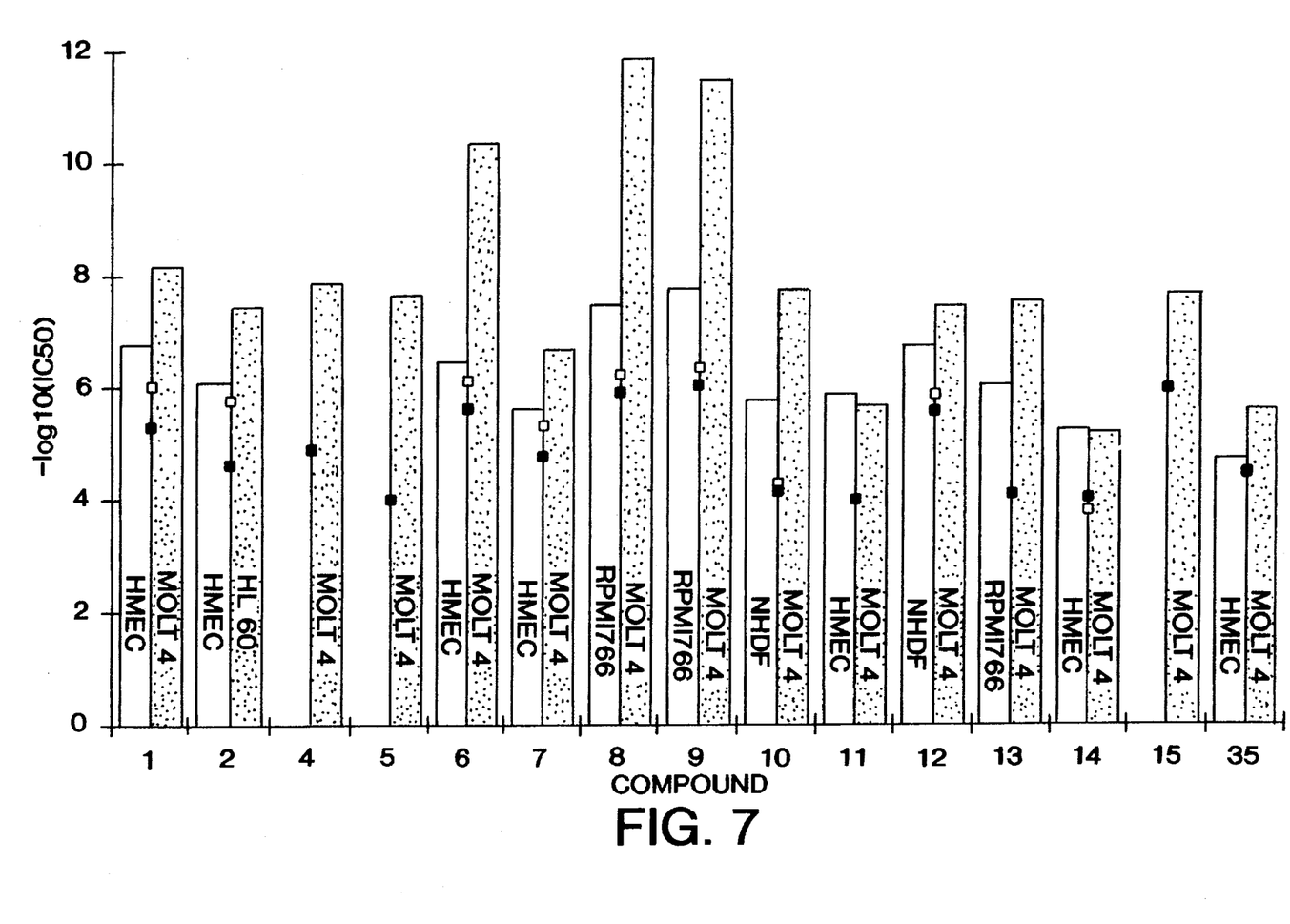

FIG. 7 shows the IC$_{50}$ values of several synthesized compounds reflecting their potencies against transformed and normal cells. It is noteworthy that the relative potencies of these compounds correlate well with their relative abilities to cleave supercoiled DNA. Thus disulfide 9 and p-nitrobenzoate 6 were amongst the most potent calicheamicinone mimics, with comparable potencies to that of calicheamicinone (8). Plausible explanations for the low cytotoxicity of the enediyne-desoxymethasone conjugate 5 may be that the steroid conjugate is not recognizable by the glucocorticoid receptor or that the glucocorticoid receptor-DNA complex does not properly position the enediyne moiety on the target for effective DNA cleavage.

The IC$_{50}$ values for the p-nitrobenzoate enediyne 6 and thioacetate 7 are compared with those of calicheamicinone (8) and calicheamicins $\gamma_1^I$ and $\theta_1^I$ in Table 1. It is clear from these data that while comparable cytotoxicities to calicheamicinone (8) can be obtained through significant simplification of the structure of the enediyne moiety, the effect of the oligosarcharide portion of calicheamicin cannot be matched by any of the designed simplifications. Comparing the potencies of 8 vs calicheamicin $\gamma_1^I$ and 7 vs calicheamicin $\theta_1^I$ (Table 1), it is reasonable to project that attachment of 6 to the oligosaccharide portion of calicheamicin or other carriers should increase its potency and/or selectivity.

Mechanism of Action.

The strong correlation between the ability of the synthesized enediynes to cause DNA cleavage and cytotoxicity suggest DNA damage as the cause of cell death by these compounds. To gain further insight into the mechanism of action of these enediynes, cells were examined for signs of apoptosis according to the method of R. E. Ellis et al. *Annu. Rev. Cell. Biol* (1991):vol. 7, pp 663–698, following exposure to compound 6, chosen as a representative of this class.

However, upon exposure of Molt-4 leukemia cells to 6 only moderate apoptosis (<20% of the cells at ($10^{-7}$ M)) was observed in contrast to the strong apoptosis indicated by calicheamicin $\theta_1^I$ at the same concentration.

It is noteworthy that all calicheamicinone mimics synthesized and tested showed predominantly single strand DNA cuts. This observation is in contrast to calicheamicins $\gamma_1^I$ and $\theta_1^I$, both of which are known to induce predominantly double strand DNA damage, according to the method of J. N. Haseltine et al., supra and of P. C. Dedon, *Biochemistry* (1993):vol. 32, pp 3617–3622. This difference correlates well with the observed cytotoxicity and ability of these compounds to cause apoptosis, the molecules with the binding domain exhibiting significantly higher potencies in both assays. Thus, it seems reasonable to suggest that, at least in the case of the enediyne type of DNA damaging agents, the propensity of a compound to induce apoptosis is proportional to its ability to cause double strand cuts of the genetic material. Apparently, the inability of cells to repair such drastic damage leads to initiation of apoptosis, whereas repair of single strand cuts may save cells from death.

Materials and methods

General Techniques.

NMR spectra were recorded on a Bruker AMX-500 instrument. The following abbreviations were used to designate the multiplicities:s, singlet; d, doublet; t, triplet; q, quartet; m, multiplet; b, broad; ohs, obscured. IR spectra were recorded on a Perkin-Elmer 1600 series FT-IR spectophotometer. Optical rotations were recorded using a Perkin-Elmer 241 polarimeter. High-resolution mass spectra (HRMS) were recorded on a VG ZAB-ZSE mass spectrometer under fast atom bombardment (FAB) conditions.

All reactions were monitored by thin-layer chromatography (TLC) carried out on 0.25 mm E. Merck silica gel plates (60F-254) using UV light, 7% ethanolic phosphomolybdic acid, or p-anisaldehyde solution and heat as a developing agent. E. Merck silica gel (60, particle size 0.040–0.063 mm) was used for flash column chromatography. Tetrahydrofuran (THF) was distilled from sodium-benzophenone and methylene choride, benzene and toluene were distilled from calcium hydride.

All reactions were carried out under argon atmosphere with anhydrous, freshly distilled solvents under anhydrous conditions, unless otherwise noted. Yields refer to chromatographically and spectroscopically ($^1$H NMR) homogeneous materials, unless otherwise stated.

Preparation of compounds.

Compounds 17 and 18:A solution of diol 16 [26] (188 mg, 386 μmol) in CH$_2$Cl$_2$ (10 mL) was treated at $-15°$ C. with pyridine (188 μL, 2.3 mmol) and benzoyl chloride (58 μL, 0.5 mmol). After 1 h, additional benzoyl chloride (58 μL, 0.5 mmol) was added to the reaction mixture. The progress of the reaction was monitored closely by TLC and, as soon as all starting material was consumed (30 min.), the reaction was quenched by addition of MeOH (0.5 mL), the cooling bath was removed, and the reaction mixture was allowed to reach room temperature. The solution was poured into a saturated aqueous solution of CuSO$_4$ (15 mL) and washed with additional saturated aqueous solution of CuSO$_4$ (2×15 mL). The combined aqueous extracts were back extracted with CH$_2$Cl$_2$ (2×15 mL) and the combined organic extracts were washed with brine (15 mL), dried (Na$_2$SO$_4$), concentrated, and purified by flash chromatography (60% Et$_2$O in petroleum ether) to give, in order of elution, dibenzoate 18 (70.1 mg, 26%) and monobenzoate 17 (155.6 mg, 68%).

17:white foam; R$_f$=0.13 (70% Et$_2$O in petroleum ether); [α]$^{25}_D$–270 (c 0.36, CH$_2$Cl$_2$); IR (neat) $v_{max}$ 3400, 3090, 3070, 3034, 2955, 2876, 1961, 1815, 1722, 1271, 1225, 1166, 1110 cm$^{-1}$; $^1$HNMR (500 MHz, C$_6$D$_6$) δ8.08–8.06 (m, 2 H, Bz), 7.07–7.04 (m, 1 H, Bz), 6.99–6.97 (m, 2 H, Bz), 6.74 (dd, J=4.94, 7.58 Hz, 1 H, C=CHCH$_2$), 6.17 (b s, 1 H, NHCOOCH$_3$), 6.04 (d, J=5.0 Hz, 1 H, CHOH), 5.71 (b d, J=10.5 Hz, 1 H, CHHOBz), 5.46–5.35 (b, ohs, 1 H, CHHOBz), 5.39–5.35 (m, 2 H, CH=CH), 3.99 (b s, 1 H, OH), 3.27–3.16 (m, 4 H, ethylene ketal), 3.23 (s, 3 H, NHCOOCH$_3$), 2.70 (d, J= 13.77 Hz, 1 H, CHH-eq), 2.44 (d, J=13.80 Hz, 1 H, CHH-ax), 1.09 (t, J=7.9 Hz, 9 H, Si(CH$_2$CH$_3$)$_3$), 0.92–0.80 (m, 6 H, Si(CH$_2$CH$_3$)$_3$); $^{13}$C NMR (125 MHz, C$_6$D$_6$) δ166.35, 154.95, 139.21, 132.35, 131.98, 131.32, 130.01, 124.27, 123.96, 123.35, 105.25, 101.79, 86.30, 85.96, 65.15, 65.12, 64.99, 64.23, 52.75, 7.40, 6.67; FAB HRMS (NBA/CsI) m/e 724.1351 (M+Cs$^+$) calcd for C$_{32}$H$_{37}$NO$_8$Si:724.1343.

18:Pale yellow foam; R$_f$=0.16 (50% Et$_2$O in petroleum ether); [α]$^{25}_D$–43.0 (c0.575, CH$_2$Cl$_2$); IR (neat) $v_{max}$ 3394, 3032, 3325, 2955, 2877, 1721, 1491, 1454, 1315, 1272, 1172 cm$^{-1}$; $^1$H NMR (500 MHz, C$_6$D$_6$) δ8.45 (d, J=7.25 Hz, 2 H, Bz), 8.02 (d, J= 7.12 Hz, 2 H, Bz), 7.58 (d, J= 1.33 Hz, 1 H, Bz), 7.18 (obs, 1 H, Bz), 7.13–7.07 (m, 2 H, Bz), 7.00 (dd, J=7.45, 7.84 Hz, 2 H, Bz), 6.87 (dd, J=4.42, 8.06 Hz, 1 H, C=CHCH$_2$), 6.28 (b s, 1 H, CHOBz), 5.60 (dd, J=4.38, 9.25 Hz, 1 H, C=CHCHH), 5.44 (d, J=9.44 Hz, 1 H, CH=CHC≡CCH), 5.39 (dd, J= 8.08, 13.65 Hz, 1 H, C=CHCHH), 5.32 (dd, J=1.41, 9.43 Hz, 1 H, CH=C≡CCH), 3.33 (s, 3 H, NHCOOCH$_3$), 3.31–3.22 (m, 4 H, ethylene ketal), 2.84 (d, J= 13.7 Hz, 1 H, CHH-eq), 2.55 (d, J=13.7 Hz, 1 H, CHH-ax), 1.20–1.16 (m, 9 H, Si(CH$_2$CH$_3$)$_3$), 0.98–0.93 (m, 6 H, Si(CH$_2$CH$_3$)$_3$); $^{13}$C NMR (125 MHz, C$_6$D$_6$) δ165.96, 165.88, 153.60, 139.58, 132.86, 132.14, 130.77, 130.24, 130.21, 130.14, 129.70, 124.11, 123.92, 123.34, 105.13, 103.24, 99.25, 86.59, 85.54, 70.87, 65.23, 64.96, 64.84, 64.53, 52.51, 52.34, 29.92, 7.19, 6.46; FAB HRMS (NBA/CsI) m/e 828.1570, (M+Cs$^+$) calcd for C$_{39}$H$_{41}$NO$_9$Si: 828.1605.

Compound 19:A solution of monobenzoate 17 (34.8 mg, 58.9 μmol) in CH$_2$Cl$_2$ (0.6 mL) was treated with DMAP (88 mg, 0.72 mmol) and glutaric anhydride (58 mg, 0.51 mmol) at room temperature. As soon as all starting material was consumed (2.5 h), DCC (109 mg, 0.53 mmol) and p-nitrophenol (74 mg, 0.53 mmol) were added to the reaction mixture. After 2 h the turbid reaction mixture was applied directly to a chromatography column and purified (70% Et$_2$O in petroleum ether) to give diester 19 (22.2 mg, 46%):pale yellow solid; $R_f$=0.5 ($Et_2O$); $[α]^{25}{}_D$–106 (c0.47, $CH_2Cl_2$); IR (neat) $ν_{max}$ 3315, 2920, 2848, 1739, 1718, 1618, 1582, 1524, 1490, 1452, 1344, 1313, 1271, 1216, 1115 cm$^{-1}$; $^1$H NMR (500 MHz, $C_6D_6$) δ8.12–8.10 (m, 2 H, Ar), 7.78–7.76 (m, 2 H, Ar), 7.24 (b s, 1 H, NHCOOCH$_3$), 7.13–7.11 (m, 1 H, Ar), 7.07–7.04 (m, 2 H, Ar), 6.89 (dd, J=3.69, 8.27 Hz, 1 H, C=CHCH$_2$), 6.75–6.73 (m, 2 H, Ar), 6.16 (b s, 1 H, CHOCOCH$_2$), 5.66 (dd, J= 3.54, 14.22 Hz, 1 H, CHHOBz), 5.43 (d, J= 9.44 Hz, 1 H, CH=CHC≡CCH), 5.38 (dd, J=8.31, 14.19 Hz, 1 H, CHHOBz), 5.35 (dd, J= 1.20, 9.41 Hz, 1 H, CH=CHC≡CCH), 3.34 (s, 3 H, NHCOOCH$_3$), 3.29–3.17 (m, 4 H, ethylene ketal), 2.82 (d, J=13.80 Hz, 1 H, CHH-eq), 2.68 (dt, J=7.25, 16.46 Hz, 1 H, CH$_2$), 2.55 (d, J= 13.78 Hz, 1 H, CHH-ax), 2.43–2.38 (m, 3 H, CH$_2$), 2.04–1.99 (m, 2 H, CH$_2$), 1.19–1.16 (m, 9 H, Si(CH$_2$CH$_3$)$_3$), 0.95–0.90 (m, 6 H, Si(CH$_2$CH$_3$)$_3$); $^{13}$C NMR (125 MHz, $C_6D_6$) δ171.68, 170.08, 166.57, 155.48, 154.03, 145.32, 138.85, 134.25, 132.74, 130.88, 129.88, 124.95, 124.61, 124.13, 123.51, 122.37, 105.12, 103.55, 98.87, 86.86, 85.69, 71.03, 65.37, 65.16, 65.14, 65.00, 52.74, 52.09, 33.10, 33.04, 30.18, 26.01, 25.32, 20.12, 7.42; FAB HRMS (NBA/CsI) m/e 959.1824, (M+Cs$^+$) calcd for $C_{43}H_{46}N_2O_{13}Si$:959.1820.

Compound 20: A solution of monobenzoate 17 (43 mg, 73 μmol) in $CH_2Cl_2$ (1 mL) was treated at ambient temperature with DMAP (25 mg, 0.12 mmol) and glutaric anhydride (24 mg, 0.21 mmol). After 6 h the reaction mixture was applied directly on a chromatography column and it was purified ($Et_2O$ →5% MeOH/$Et_2O$) to give acid 20 (35.7 mg, 69%):pale yellow foam; $R_f$=0.26 ($Et_2O$); $[α]^{25}{}_D$–168 (c1.87, $CH_2Cl_2$); IR (neat) $ν_{max}$ 3295, 3061, 2956, 2880, 2671, 1716, 1631, 1496, 1454, 1416, 1317, 1273 cm$^{-1}$; $^1$H NMR (500 MHz, CDCl$_3$) δ8.05–8.04 (m, 2 H, Bz), 7.57–7.54 (m, 1 H, Bz), 7.54–7.42 (m, 2 H, Bz), 6.54 (b s, 1 H, NHCOOMe), 6.38 (dd, J=4.05, 8.24 Hz, 1 H, C=CHCH$_2$), 6.31 (s, 1 H, CHOCOCH$_2$), 5.92 (d, J=9.41 Hz, 1 H, CH=CHC≡CCH), 5.82 (dd, J=1.33, 9.48 Hz, 1 H, CH=CHC≡CCH), 5.24 (dd, J=3.82, 13.93 Hz, 1 H, CHHOBz), 4.98 (dd, J=8.29, 13.92 Hz, 1 H, CHHOBz), 4.11–4.06 (m, 1 H, ethylene ketal), 4.00–3.97 (m, 2 H, ethylene ketal), 3.96–3.86 (m, 1 H, ethylene ketal), 3.72 (s, 3 H, NHCOOCH$_3$), 2.69–2.63 (m, 1 H, CHHCOOH), 2.58 (d, J= 13.70 Hz, 1 H, CHH-eq), 2.59–2.53 (m, 1 H, CHH-COOH), 2.51–2.43 (m, 2 H, CHOCOCH$_2$), 2.23 (d, J=13.66 Hz, 1 H, CHH-ax), 2.08–1.98 (m, 2 H, CH$_2$CH$_2$CH$_2$), 1.01 (t, J=7.90 Hz, 9 H, Si(CH$_2$CH$_3$)$_3$), 0.77 (m, 6 H, Si(CH$_2$CH$_3$)$_3$); $^{13}$C NMR (125 MHz, CDCl$_3$) δ178.12, 177.64, 171.88, 166.62, 154.0, 138.15, 132.85, 130.26, 129.59, 128.30, 124.77, 123.34, 123.02, 104.96, 102.30, 97.30, 86.61, 84.92, 70.69, 65.42, 64.72, 64.55, 53.27, 51.43, 33.03, 32.74, 19.82, 7.05, 6.16; FAB HRMS (NBA/CsI) m/e 838.1665, (M+ Cs$^+$) calcd for $C_{37}H_{43}NO_{11}Si$:838.1660.

Compound 5: A mixture of acid 4 (27 mg, 49 μmol) and desoxymethasone (47 mg, 0.12 mmol) was azeotroped (benzene, 2×2 mL), treated in $CH_2Cl_2$ (1 mL) with DCC (15 mg, 74 μmol) and DMAP (3 mg, 25 μmol) and stirred at room temperature for 2 h. The reaction mixture was purified directly by preparative TLC (20% acetone in benzene) to yield chimeric ester 5 (23 mg, 53%):white solid; $R_f$=0.48 (20% acetone in benzene); $[α]^{25}{}_D$–158 (c0.48, $CH_2Cl_2$); IR (neat) $ν_{max}$ 3434, 3368, 2948, 2874, 1720, 1662, 1609, 1500, 1450, 1346, 1273, 1241, 1183, 1135 cm$^{-1}$; $^1$HNMR (500 MHz, CDCl$_3$) δ7.98 (dd, J=1.27, 8.32 Hz, 2 H, Bz), 7.53–7.50 (m, 1 H, Bz), 7.39–7.36 (m, 2 H, Bz), 7.05 (d, J=10.12 Hz, 1 H, desoxymethasone H-1), 6.86 (b s, 1 H, NHCOOCH$_3$), 6.68 (d, J=1.53 Hz, 1 H, CHOCO), 6.38 (dd, J=3.54, 8.93 Hz, 1 H, C=CHCH$_2$), 6.20 (dd, J=1.82, 10.11 Hz, 1 H, des. H-2), 6.03 (s, 1 H, des. H-4), 5.86 (d, J=9.49 Hz, 1 H, CH=CHC≡CCH), 5.82 (dd, J=1.56, 9.48 Hz, 1 H, CH=CHC≡CCH), 5.29 (dd, J=3.52, 13.78 Hz, 1 H, CHHOBz), 4.85 (dd, J=8.81, 13.62 Hz, 1 H, CHHOBz), 4.83 (AB q, J=17.52 Hz, Δν=53.53 Hz, 2 H, des. H-21), 4.19 (b d, J=8.53 Hz, 1 H, des. H-11), 3.69 (s, 3 H, NHCOOCH$_3$), 3.51 (b s, 1 H, OH), 3.19 (d, J=16.89 Hz, 1 H, CHH-eq), 3.01–2.97 (m, 1 H, des.), 2.75 (d, J= 16.89 Hz, 1 H, CHH-ax), 2.63–2.24 (m, 10 H, 2 x (OCOCH$_2$) and des.), 2.07–2.01 (m, 2 H, (OCOCH$_2$)$_2$CH$_2$), 1.74–1.61 (m, 5 H, des.), 1.45 (s, 3 H, des. CH$_3$), 1.18 (b s, 1 H, des.), 1.15–1.10 (m, 1 H, des.), 0.97 (s, 3 H, des. CH$_3$), 0.81 (d, J=7.30 Hz, 3 H, des. CH$_3$); $^{13}$C NMR (125 MHz, CDCl$_3$) δ204.75, 191.18, 186.72, 172.75, 171.50, 166.71, 166.32, 153.87, 152.39, 137.25, 133.29, 131.15, 129.67, 128.46, 128.31, 125.43, 125.02, 124.85, 124.08, 100.92, 99.72, 99.52, 96.92, 91.16, 87.44, 84.21, 72.21, 72.12, 71.81, 68.69, 65.16, 63.93, 53.46, 53.01, 48.43, 43.96, 36.36, 35.79, 34.23, 34.07, 32.65, 32.20, 32.13, 30.97, 27.32, 22.91, 22.87, 19.94, 16.45, 14.62; FAB HRMS (NBA/CsI) m/e 944.3270, (M+Cs$^+$) calcd for $C_{51}H_{52}NO_{14}F$:944.3270.

Compound 6: Pyridine (25 μL, 0.3 mmol) and DMAP (6 mg, 0.5 μmol) were added to a solution of diol 16 (50 mg, 0.1 mmol) in $CH_2Cl_2$ (10 mL) at –15° C. p-Nitrobenzoyl chloride (26 mM in $CH_2Cl_2$) was added dropwise and in two portions (0.13+0.1 mmol, 1 h interval) until almost all starting material was consumed and then the reaction was qluenched by MeOH (0.5 mL). After standard aqueous workup, the reaction mixture was purified by flash column chromatography (50→100% $Et_2O$/petroleum ether) to give the fully protected mono-p-nitrobenzoate (42 mg, 66%). Small amounts of dibenzoate (4 mg, 0.5%) and unreacted diol 16 (8 mg, 30%) were also isolated. Mono-p-nitrobenzoate:foam; $R_f$=0.47 ($Et_2O$); $[α]^{25}{}_D$–216 (c1.40, $CH_2Cl_2$); IR (neat) $ν_{max}$ 3326, 2956, 2931, 2877, 1723, 1606, 1528, 1501, 1461, 1343, 1274 cm$^{-1}$; $^1$HNMR (500 MHz, CDCl$_3$) δ8.27 (d, J=8.92 Hz, 2 H, Ar), 8.23 (d, J=8.94 Hz, 2 H, Ar), 6.50 (b s, 1 H, NHCOOCH$_3$), 6.35 (dd, J=5.40, 7.64 Hz, 1 H, C=CHCH$_2$), 5.89 (d, J=9.50 Hz, 1 H, CH=CHC≡CCH), 5.84 (dd, J=1.04, 9.46 Hz, 1 H, CH=CHC≡CCH), 5.71 (d, J=4.77 Hz, 1 H, CHOH), 5.34 (dd, J=5.13, 13.79 Hz, 1 H, CHHOCOAr), 5.20 (b m, 1 H, CHHOCOAr), 4.03–3.91 (m, 4 H, ethylene ketal), 3.77 (s, 3 H, NHCOOCH$_3$), 2.55 (d, J=14.00 Hz, 1 H, CHH-eq), 2.25 (d, J=13.97 Hz, 1 H, CHH-ax), 1.00 (t, J=7.88 Hz, 9 H, Si(CH$_2$CH$_3$)$_3$), 0.83–0.70 (m, 6 H, Si(CH$_2$CH$_3$)$_3$); $^{13}$C NMR (125 MHz, CDCl$_3$) δ164.56, 155.12, 150.34, 140.16, 136.13, 130.81, 123.40, 104.77, 99.85, 86.32, 85.59, 65.57, 65.37, 65.20, 63.56, 53.42, 50.39, 29.71, 7.08, 6.12; FAB HRMS (NBA/NaI) m/e 659.2050, (M+Na$^+$) calcd for $C_{32}H_{36}N_2O_{10}Si$:659.2037.

A solution of the monobenzoate 6 (42 mg, 66 μmol) in THF (1.4 mL) and $H_2O$ (4 drops) was treated with TsOH·$H_2O$ (30 mg, 0.15 mmol) and the mixture was stirred at ambient temperature for 36 h. The reaction mixture was diluted with $CH_2Cl_2$, passed through a short column of $Na_2SO_4$ and purified by preparative TLC (20% acetone in $CH_2Cl_2$) to give enone 6 (14 mg, 45%):colorless solid; $R_f$=0.63 (20% acetone in $CH_2Cl_2$); $[α]^{25}{}_D$–910 (c0.12, $CH_2Cl_2$); IR (neat) $ν_{max}$ 3358, 2919, 1719, 1679, 1525, 1344, 1274 cm$^{-1}$; $^1$H NMR (500 MHz, CDCl$_3$) δ8.29–8.22 (m, 4 H, Ar), 7.00 (b s, 1 H, NHCOOCH$_3$), 6.43 (dd, J=4.27, 8.11 Hz, 1 H, C=CHCH$_2$), 6.01 (b d, J=4.72 Hz, 1 H, CHOH), 5.93 (dd, J=1.37, 9.48 Hz, 1 H, CH=CHC≡CCH), 5.89 (d, J= 9.48 Hz, 1 H, CH=CHC≡CCH), 5.36 (dd, J=4.23, 14.24 Hz, 1 H, CHHOCOAr), 5.19 (dd, J= 8.14, 14.23 Hz, 1 H, CHHOCOAr), 3.80 (s, 3 H, NHCOOCH$_3$), 3.65 (b s, 1 H, OH), 3.23 (d, J=17.04 Hz, 1 H, CHH-eq), 3.02 (b s, 1 H, OH), 2.80 (d, J=17.03 Hz, CHH-ax); $^{13}$C NMR (125 MHz, CDCl$_3$) δ190.96, 164.60, 154.78, 150.55, 137.72, 135.51, 130.86, 130.17, 128.34, 124.56, 123.73, 123.54, 99.91, 99.56, 87.99, 85.21, 72.27, 53.59, 51.71, 29.71; FAB HRMS (NBA/CsI) m/e 611.0055, (M+Cs$^+$) calcd for C$_{24}$H$_{18}$N$_2$O$_9$:611.0067.

Compound 22: A solution of thioacetate 21 [26] (9 mg, 14 μmol) in CH$_2$Cl$_2$ (2 mL) was treated with DIBAL (100 μL, 1.0 M in CH$_2$Cl$_2$, 100 μmol) at −78° C. After stirring at this temperature for 30 min, the excess reagent was quenched by dropwise addition of MeOH (2 mL) and the reaction mixture was allowed to warm up to room temperature. MeSS-COOMe (66 μL, 0.89 M in MeOH, 59 μmol) was added and the reaction mixture was stirred at room temperature for 12 h. Following dilution with EtOAc (5 mL), saturated aqueous solution of Rochelle salt (sodium potassium tartrate, 2 mL) was added and stirring was continued for 45 min. Standard aqueous work up and flash column chromatography (30→ 50% Et$_2$O in petroleum ether) gave disulfide 22 (6.3 mg, 70%):colorless oil; R$_f$=0.29 (50% Et$_2$O in petroleum ether); [α]$^{25}$$_D$−196 (c0.525, CH$_2$Cl$_2$); IR (neat) v$_{max}$ 3356, 2954, 2915, 2876, 1738, 1490, 1458, 1413, 1223 cm$^{-1}$; $^1$H NMR (500 MHz, C$_6$D$_6$) δ6.60 (dd, J= 4.17, 10.98 Hz, 1 H, C=CHCH$_2$), 6.31 (b s, 1 H, CHOSi), 6.09 (b s, 1 H, NHCOOCH$_3$), 5.50 (d, J=9.39 Hz, 1 H, CH=CHC≡CH), 5.38 (dd, J=1.63, 9.38 Hz, 1 H, CH=CHC≡CH), 4.31 (dd, J=11.34, 13.47 Hz, 1 H, CHHSSCH$_3$), 3.60 (dd, J=4.06, 13.88 Hz, 1 H, CHHSSCH$_3$), 3.39 (b s, 3 H, NHCOOCH$_3$), 3.35–3.26 (m, 4 H, ethylene ketal), 2.73 (AB q, J=12.81 Hz, Δv=28.17 Hz, 2 H, CH$_2$), 2.44 (b s, 3 H, SSCH$_3$), 1.20 (t, J=7.9 Hz, 9 H, OSi(CH$_2$CH$_3$)$_3$), 1.13 (m, J=7.7 Hz, 9 H, OSi(CH$_2$CH$_3$)$_3$), 0.98–0.81 (m, 12 H, 2 x (OSi(CH$_2$CH$_3$)$_3$)); $^{13}$C NMR (125 MHz, C$_6$D$_6$) δ139.19, 125.86, 124.39, 123.06, 106.43, 102.38, 84.94, 72.69, 65.33, 64.59, 54.37, 52.36, 30.18, 22.75, 7.49, 7.07, 6.79, 5.17; FAB HRMS (NBA/CsI) m/e 796.1599, (M+Cs$^+$) calcd for C$_{32}$H$_{49}$NO$_6$S$_2$Si$_2$:796.1594.

(23) A solution of thioacetate 21 (14.4 mg, 21.8 μmol) in MeOH (3 mL) was treated with NaOMe (5 mg, 93 μmol) and the resulting mixture was stirred at 0° C. for 3 h. 2,2'-Dipyridyl disulfide (aldrithiol-2, 24 mg, 109 μmol) was added to the reaction mixture and stirring was continued at 0° C. for 3 h. After standard aqueous workup the reaction mixture was initially purified by flash column chromatography (50→70% Et$_2$O in petroleum ether) and, subsequently, by reverse phase HPLC (C18 column, 20% CH$_3$CN in H$_2$O for 7 min, then 100% CH$_3$CN over 10 min; retention time 19.13 min) to yield the disulfide 23 (10.6 mg, 66%):colorless film; R$_f$=0.37 (70% Et$_2$O in petroleum ether); [α]$^{25}$$_D$−130 (c0.42, CH$_2$Cl$_2$); IR (neat) v$_{max}$ 3354, 2954, 2878, 1735, 1570, 1493, 1453, 1416, 1319, 1227 cm$^{-1}$; $^1$H NMR (500 MHz, C$_6$D$_6$) δ8.32 (d, J=4.71 Hz, 1 H, Pyr), 7.88 (d, J=7.59 Hz, 1 H, Pyr), 7.2 (ohs, Pyr), 6.70 (dd, J=5.24, 10.04 Hz, 1 H, C=CHCH$_2$), 6.51 (dd, J=4.83, 7.29 Hz, 1 H, Pyr), 6.31 (s, 1 H, NHCOOCH$_3$), 6.06 (b s, 1 H, CHOSi), 5.47 (d, J=9.40 Hz, 1 H, CH=CHC≡CH), 5.37 (dd, J=1.59, 9.36 Hz, 1 H, CH=CHC≡CH), 4.28 (dd, J=10.11, 13.42 Hz, 1 H, CHHSSPyr), 3.99 (dd, J=5.24, 13.48 Hz, 1 H, CHH-SSPyr), 3.39 (s, 3 H, NHCOOCH$_3$), 3.34–3.31 (m, 2 H, ethylene ketal), 3.26–3.24 (m, 2 H, ethylene ketal), 2.71 (d, J= 13.14 Hz, 1 H, CHH-eq), 2.42 (d, J=13.16 Hz, 1 H, CHH-ax), 1.19–1.16 (m, 9 H, Si(CH$_2$CH$_3$)$_3$), 1.11–1.08 (m, 9 H, Si(CH$_2$CH$_3$)$_3$), 0.94–0.79 (m, 12 H, 2 x (Si(CH$_2$CH$_3$)$_3$)); $^{13}$C NMR (125 MHz, C$_6$D$_6$) δ161.70, 149.54, 138.92, 136.73, 124.26, 124.15, 123.19, 119.95, 119.63, 106.03, 102.48, 85.56, 85.04, 72.21, 65.21, 64.75, 64.55, 53.74, 52.38, 40.33, 7.48, 7.07, 6.74, 5.15; FAB HRMS (NBA/CsI) m/e 859.1713, (M+Cs$^+$) calcd for C$_{36}$H$_{50}$N$_2$O$_6$S$_2$Si$_2$:859.1703.

Compound 11: A solution of alcohol 24 (24.5 mg, 41 μmol) in THF (5 mL) was treated at 0° C. with pyridinium poly(hydrogen fluoride) (100 μL). The reaction mixture was allowed to warm up to ambient temperature over 4 h and, upon completion of the reaction, it was diluted with EtOAc (10 mL) and washed with a saturated aqueous solution of NaHCO$_3$ (3×10 mL). The combined aqueous extracts were back extracted with EtOAc (3×10 mL) and the combined organic layers were washed with brine (10 mL), dried (Na$_2$SO$_4$), concentrated and purified by flash chromatography (EtOAc) to yield triol 11 (15 mg, 96%):white amorphous solid; R$_f$= 0.12 (EtOAc); [α]$^{25}$$_D$−340 (c0.75, CH$_2$Cl$_2$); IR (neat) v$_{max}$ 3378, 2956, 2928, 2894, 1712, 1631, 1501, 1455, 1324, 1243, 1157, 1117 cm$^{-1}$; $^1$HNMR (500 MHz, CDCl$_3$) δ6.57 (b s, 1 H, NHCOOCH$_3$), 6.30 (dd, J=7.23, 7.51 Hz, 1 H, C=CHCH$_2$), 5.73 (s, 2 H, CH=CH), 5.51 (b s, 1 H, C≡CCHOH), 4.70 (b s, 1 H, OH), 4.22 (dd, J=8.07, 13.26 Hz, 1 H, C=CHCHH), 4.12 (b dd, J=6.59, 13.09 Hz, 1 H, C=CHCHH), 3.95–3.92 (m, 1 H, ethylene ketat), 3.91–3.82 (m, 3 H, ethylene ketal), 3.68 (s, 3 H, NHCOOCH$_3$), 3.31 (b s, 1 H, OH), 2.83 (b s, 1 H, OH), 2.47 (d, J= 14.31 Hz, 1 H, CHH-eq), 2.21 (d, J= 14.31 Hz, 1 H, CHH-ax); $^{13}$C NMR (125 MHz, CDCl$_3$) δ155.24, 141.30, 133.93, 128.31, 126.61, 123.53, 104.76, 103.32, 98.56, 86.04, 85.33, 68.60, 65.90, 65.08, 63.16, 60.14, 49.06, 29.68; FAB HRMS (NBA/CsI) m/e 506.0211, (M+Cs$^+$) calcd for C$_{19}$H$_{19}$NO$_7$:506.0216.

Compound 25: A solution of alcohol 24 (51.0 mg, 84.7 μmol) in CH$_2$Cl$_2$ (1.8 mL) was treated with pyridine (28 μL, 0.35 mmol), acetic anhydride (24 μL, 0.25 mmol), and DMAP (5 mg, 42 μmol) at 0° C. and the mixture was stirred at room temperature for 2 h. The reaction mixture was purified directly by preparative TLC (70% Et$_2$O in petroleum ether) to yield acetate 25 (50.1 mg, 92%):colorless syrup; R$_f$=0.68 (80% Et$_2$O in petroleum ether); [α]$^{25}$$_D$−266 (c0.865, CH$_2$Cl$_2$); IR (neat) v$_{max}$ 3349, 2954, 2878, 1737, 1494, 1323, 1232 cm$^{-1}$; $^1$H NMR (500 MHz, C$_6$D$_6$) δ6.65 (dd, J=3.33, 9.07 Hz, 1 H, C=CHCH$_2$), 6.35 (s, 1 H, NHCOOCH$_3$), 6.06 (b s, 1 H, CHOSi), 5.48 (d, J=9.40 Hz, 1 CH=CHC≡CH), 5.44–5.35 (ohs, 1 H, CHHOAc), 5.39 (dd, J= 1.55, 9.39 Hz, 1 H, CH=CHC≡CH), 5.16 (dd, J= 9.12, 13.91 Hz, 1 H, CHHOAc), 3.49–3.25 (m, 4 H, ethylene ketal), 3.41 (s, 3 H, NHCOOCH$_3$), 2.74 (d, J= 13.19 Hz, 1 H, CHH-eq), 2.49 (d, J= 13.20 Hz, 1 H, CHH-ax), 1.29–1.09 (m, 18 H, 2 x (Si(CH$_2$CH$_3$)$_3$)), 1.05–0.89 (m, 12 H, 2 x (Si(CH$_2$CH$_3$)$_3$)); $^{13}$C NMR (125 MHz, C$_6$D$_6$) δ170.20, 138.36, 124.14, 123.34, 106.04, 102.20, 85.49, 85.26, 72.14, 65.30, 64.94, 64.81, 64.58, 53.40, 52.47, 20.49, 7.41, 7.10, 6.73, 5.03; FAB HRMS (NBA/CsI) m/e 776.2088, (M+Cs$^+$) calcd for C$_{33}$H$_{49}$NO$_8$Si$_2$:776.2051.

Compound 26: A solution of 2-phenylthioethanol (3 g, 19 mmol) in benzene (5 mL) was added dropwise, at room temperature, to a solution of phosgene (1 mL, 1.9 M toluene, 1.9 mmol). After stirring for 3 h the excess phosgene and solvents were removed under vacuum to give 2-phenylthioethyl-chloroformate as a yellow oil which was used without further purification. A solution of alcohol 24 (27 mg, 45 μmol) and DMAP (38 mg, 0.31 mmol)in CH$_2$Cl$_2$ (5 mL) was treated, at 0° C., with 2-phenylthioethyl-chloroformate (38 mg, 0.18 mmol) and the mixture was stirred for 4 h. The reaction mixture was poured into brine (10 mL), extracted with CH$_2$Cl$_2$ (3×5 mL), dried (Na$_2$SO$_4$), concentrated, and purified by preparative TLC (20% EtOAc in benzene) to give carbonate 26 (30.7 mg, 88%):pale yellow oil; $R_f$= 0.69 (20% EtOAc in benzene); $[\alpha]^{25}_D$ –150 (c0.20, $CH_2Cl_2$); IR (neat) $v_{max}$ 2954, 2876, 1738, 1721, 1492, 1458, 1257, 1164 cm$^{-1}$; $^1$H NMR (500 MHz, CDCl$_3$) 7.41–7.40 (m, 2 H, Ph), 7.40–7.27 (m, 2 H, Ph), 7.26–7.19 (m, 1 H, Ph), 6.10 (rid, J=3.27, 9.02 Hz, 1 H, C=CHCH$_2$), 5.87 (d, J=9.71 Hz, 1 H, CH=CHC≡CCH), 5.77 (b d, J=9.71 Hz, 1 H, CH=CHC≡CCH), 5.77 (b s, 1 H, CHOSi), 4.88 (dd, J=3.33, 13.52 Hz, 1 H, CHHOCO), 4.79 (dd, J=9.04, 13.54 Hz, 1 H, CHHOCO), 4.28–4.23 (m, 2 H, OCOCH$_2$CH$_2$SPh), 4.10–4.07 (m, 1 H, ehtylene ketal), 3.99–3.91 (m, 2 H, ethylene ketal), 3.88–3.84 (m, 1 H, ethylene ketal), 3.18 (dd, J=7.23, 7.40 Hz, 2 H, OCOCH$_2$CH$_2$SPh), 2.48 (d, J=13.24 Hz, 1 H, CHH-eq), 2.11 (d, J=13.25 Hz, 1 H, CHH-ax), 1.00–0.96 (m, 18 H, 2 x (Si(CH$_2$CH$_3$)$_3$)), 0.79–0.67 (m, 12 H, 2 x (Si(CH$_2$ CH$_3$)$_3$)); $^{13}$C NMR (125 MHz, CDCl$_3$) δ154.70, 138.17, 129.81, 129.07, 126.58, 124.11, 122.91, 122.46, 105.72, 68.04, 65.75, 65.52, 65.22, 63.71, 52.34, 31.95, 29.70, 7.07, 6.72, 6.16, 4.53; FAB HRMS (NBA/CsI) m/e 914.2180, (M+Cs$^+$) calcd for C$_{40}$H$_{55}$NO$_9$SSi:914.2190.

Compound 27:A solution of carbonate 26 (30.7 mg, 39 μmol)in CH$_2$Cl$_2$ (20 mL) was treated, at ambient temperature, with mCPBA (27 mg, 0.16 mmol) and the mixture was stirred for 2 h. The solvent was removed and the reaction mixture was purified by preparative TLC (20% EtOAc/ CGHG) to give sulfone 27 (30 mg, 94%):pale yellow oil; $R_f$=0.43 (20% EtOAc in benzene); $[\alpha]^{25}_D$–140 (c0.16, CH$_2$Cl$_2$); IR (neat) $v_{max}$ 3396, 3057, 2956, 2920, 2877, 2853, 1747, 1738, 1676, 1490, 1454, 1325, 1262 cm$^{-1}$; $^1$H NMR (500 MHz, CDCl$_3$) δ7.86–7.84 (m, 2 H, SO$_2$Ph), 7.63–7.60 (m, 1 H, SO$_2$Ph), 7.53–7.50 (m, 2 H, SO$_2$Ph), 5.92 (dd, J=2.82, 9.05 Hz, 1 H, C=CHCH$_2$), 5.81 (d, J=9.34 Hz, 1 H, CH=CHC≡CCH), 5.70 (dd, J=1.62, 9.38 Hz, 1 H, CH=CHC≡CCH), 5.68 (d, J=1.47 Hz, 1 H, CHOSi), 4.74 (b s, 1 H, NHC, OOCH$_3$), 4.65 (dd, J=2.73, 13.33 Hz, 1 H, CHHOCO), 4.58 (b m, 1 H, CHHOCO), 4.41–4.32 (m, 2 H, OCOCH$_2$CH$_2$SO$_2$Ph), 4.05–4.02 (m, 1 H, ethylene ketal), 3.95–3.91 (m, 1 H, ethylene ketal), 3.89–3.85 (m, 1 H, ethylene ketal), 3.82–3.79 (m, 1 H, ethylene ketal), 3.66 (s, 3 H, NHCOOCH$_3$), 3.49–3.42 (m, 2 H, OCOCH$_2$CH$_2$SO$_2$Ph), 2.42 (d, J=13.24 Hz, 1 H, CHH-eq), 2.01 (d, J=13.24 Hz, 1 H, CHH-ax), 0.92–0.89 (m, 18 H, 2 x (Si(CH$_2$CH$_3$ )$_3$)), 0.70–0.60 (m, 12 H, 2 x (Si(CH$_2$CH$_3$)$_3$)); $^{13}$C NMR (125 MHz, CDCl$_3$) δ154.00, 139.06, 138.42, 134.16, 129.38, 128.31, 128.03, 124.09, 122.92, 121.91, 105.66, 100.98, 84.69, 71.46, 68.22, 65.54, 65.22, 63.67, 60.68, 54.90, 52.94, 52.45, 29.68, 7.05, 6.69, 6.14, 4.50; FAB HRMS (NBA/CsI) m/e 946.2080, (M+ Cs$^+$) calcd for C$_{40}$H$_{55}$NO$_{11}$SSi$_2$:946.2089.

Compound 28:A solution of alcohol 24 (28.7 mg, 47.6 μmol) in CH$_2$Cl$_2$ (0.5 mL) was treated at 0° C. with pyridine (38 μL, 0.48 mmol), mesyl chloride (18 μL, 0.24 mmol), and DMAP (3 mg, 24 μmol). The resulting mixture was stirred for 3 h. The reaction mixture was filtered through a short silica column, using ether as eluent, and the solvents were removed. The resulting sensitive mesylate was dissolved in DMF (0.5 mL) and NaN$_3$ (30 mg, 0.5 mmol) was added. The mixture was stirred at 50° C. for 1 h, the solvent was removed under vacuum and the residue was purified by flash column chromatography (70% Et$_2$O in petroleum ether) to give azide 28 (17 mg, 53%):colorless syrup; $R_f$=0.45 (70% Et$_2$O in petroleum ether); $[\alpha]^{25}_D$–386 (c1.14, CH$_2$Cl$_2$); IR (neat) $v_{max}$ 3302, 2955, 2879, 2089, 1731, 1497, 1461, 1415, 1326, 1234, 1167, 1101 cm$^{-1}$; $^1$H NMR (500 MHz, C$_6$D$_6$) δ7.08 (t, J=6.03 Hz, 1 H, C=CHCH$_2$), 6.38 (b s, 1 H, NHCOOCH$_3$), 5.72 (b s, 1 H, CHOSi), 5.40 (d, J=9.47 Hz, 1 H, CH=CHC≡CCH), 5.34 (dd, J=1.37, 9.46 H, 1 H, CH=CHC≡CCH), 4.52 (d, J= 5.91 Hz, 2 H, CH$_2$N$_3$), 3.47 (b s, 3 H, NHCOOCH$_3$), 3.44–3.40 (m, 4 H, ethylene ketal), 2.52 (s, 2 H, CH$_2$), 1.22–1.16 (m, 9 H, Si(CH$_2$CH$_3$)$_3$), 1.04–1.01 (m, 9 H, Si(CH $_2$CH$_3$)$_3$), 0.98–0.90 (m, 6 H, Si(CH$_2$CH$_3$)$_3$), 0.87–0.70 (m, 6 H, Si(CH$_2$CH$_3$)$_3$); $^{13}$C NMR (125 MHz, C$_6$D$_6$) δ139.38, 126.09, 123.47, 123.31, 105.84, 102.17, 101.58, 87.28, 85.69, 73.89, 65.65, 65.39, 64.79, 52.46, 49.71, 49.55, 30.16, 29.37, 7.18, 7.10, 6.40, 5.05; FAB HRMS (NBA/CsI) m/e 759.2010, (M+Cs$^+$) calcd for C$_{31}$H$_{96}$N$_4$O$_6$Si$_2$:759.2010.

Compound 29:Azide 28 (7.4 mg, 11 μmol) was taken in freshly distilled thiolacetic acid (0.4 mL) and stirred at ambient temperature for 2 h. The excess of thiolacetic acid was removed under vacuum and the resulting oil was purified by preparative TLC (70% Et$_2$O in petroleum ether) to yield acetamide 29 (3.4 mg, 48%):white powder; $R_f$=0.31 (Et$_2$O); $[\alpha]^{25}_D$–280 (c0.09, CH$_2$Cl$_2$); IR (neat) $v_{max}$ 2954, 2915, 2877, 1730, 1665, 1551, 1535, 1450, 1241 cm$^{-1}$; $^1$H NMR (500 MHz, CDCl$_3$) δ6.52 (dd, J=6.41, 6.44 Hz, 1 H, C=CHCH$_2$), 5.88 (b s, 1 H, NHCOOCH$_3$), 5.84 (d, J=9.44 Hz, 1 H, CH=CHC≡CCH), 5.76 (dd, J=1.43, 9.44 Hz, 1 H, CH=CHC≡CCH), 5.62 (b m, 2 H, CHOSi & NHCOCH$_3$), 4.43–4.39 (m, 2 H, ethylene ketal), 4.13–4.09 (m, 1 H, CHHNHCOCH$_3$), 4.02–4.00 (m, 1 H, CHHNHCOCH$_3$), 3.99–3.87 (m, 2 H, ethylene ketal), 3.71 (s, 3 H, NHCOOCH$_3$), 2.39 (d, J=13.34 Hz, 1 H, CHH-eq), 2.32 (d, J=13.33 Hz, 1 H, CHH-ax), 1.95 (s, 3 H, NHCOCH$_3$), 1.02–0.93 (m, 18 H, 2 x (Si(CH$_2$CH$_3$)$_3$)), 0.88–0.63 (m, 12 H, 2 x (Si(CH$_2$CH$_3$)$_3$)); $^{13}$C NMR (125 MHz, CDCl$_3$) δ169.35, 138.53, 128.08, 123.51, 122.97, 105.60, 86.69, 65.70, 65.22, 64.48, 52.94, 49.17, 37.38, 23.34, 7.04, 6.80, 6.01, 4.56; FAB HRMS (NBA/CsI) m/e 775.2239, (M+Cs$^+$) calcd for C$_{33}$H$_{50}$N$_2$O$_7$Si$_2$:775.2211.

Compound 31:To a solution of enamine 30 (31 mg, 73 μmol) and pyridine (60 μL, 0.74 mmol) in CH$_2$Cl$_2$ (3 mL) was added dropwise, at room temperature, oxalyl chloride (120 μL, 1.9 M in toluene, 228 μmol). After stirring for 30 min, more pyridine (60 μL, 0.74 mmol) and 2-phenylthioethanol (100 μL, 0.74 mmol) were added and the reaction mixture was stirred for further 2 h. The reaction mixture was poured into brine (15 mL) and extracted with CH$_2$Cl$_2$ (3×5 mL). The organic extracts were dried (Na$_2$SO$_4$), concentrated, and purified by flash column chromatography (10→ 20% EtOAc in benzene) to yield carbamate 31 (36 mg, 82%):colorless foam; $R_f$=0.55 (20% EtOAc in benzene); $[\alpha]^{25}_D$–455 (c1.45, CH$_2$Cl$_2$); IR (neat) $v_{max}$ 3284, 2956, 2877, 1774, 1725, 1667, 1592, 1504, 1326, 1299, 1223, 1182, 1114 cm$^{-1}$; $^1$H NMR (500 MHz, CDCl$_3$) δ7.41–7.39 (m, 2 H, Ph), 7.32–7.29 (m, 2 H, Ph), 7.24–7.22 (m, 1 H, Ph), 6.18 (s, 1 H, C=CH), 6.11 (b s, 1 H, CHO), 5.95 (b s, 1 H, NHCOO), 5.92 (d, J=9.57 Hz, 1 H, CH=CHC≡CCHO), 5.81 (b d, J=9.41 Hz, 1 H, CH=CHC≡CCHO), 4.33–4.28 (m, 2 H, ethylene ketal), 4.20–4.18 (m, 1 H, ethylene ketal), 4.18–4.07 (m, 1 H, ethylene ketal), 4.00–3.90 (m, 2 H, COOCH$_2$CH$_2$SPh), 3.16 (t, J=6.74 Hz, 2 H, COOCH$_2$CH$_2$SPh), 2.45 (d, J=13.61 Hz, 1 H, CHH-eq), 2.27 (d, J=13.60 Hz, 1 H, CHH-ax), 1.00 (t, J=7.91 Hz, 9 H, Si(CH$_2$CH$_3$)$_3$), 0.82–0.70 (m, 6 H, Si(CH$_2$CH$_3$)$_3$); $^{13}$C NMR (125 MHz, CDCl$_3$) δ162.50, 153.94, 134.72, 130.05, 129.08, 127.87, 126.72, 124.65, 123.35, 110.89, 104.71, 99.23, 96.23, 90.65, 87.95, 69.13, 68.64, 65.91, 65.27, 64.33, 45.44, 32.59, 6.90, 5.90; FAB HRMS (NBA/CsI) m/e 738.0970, (M+ Cs$^+$) calcd for C$_{32}$H$_{35}$NO$_7$SSi:738.0958.

Compound 32:A solution of lactone 31 (28 mg, 46 μmol) in CH$_2$Cl$_2$ (3 mL) was treated at –78° C. with DIBAL (100 μL, 1 M in CH$_2$Cl$_2$, 100 μmol). After stirring for 30 min at −78° C., the reaction was quenched by dropwise addition of MeOH (0.2 mL) and the cooling bath was removed. After warming to room temperature, the mixture was diluted with EtOAc (10 mL) and saturated aqueous solution of Rochelle salt (sodium potassium tartrate, 10 mL) was added. After stirring for 1 h, the organic layer was separated and the aqueous Layer was extracted with additional EtOAc (3×5 mL). The combined organic extracts were dried ($Na_2SO_4$), concentrated, and purified by preparative TLC (20% EtOAc in benzene) to yield lactol 32 (26.6 mg, ca. 4:1 mixture of epimers, 95%):colorless oil; $R_f$=0.36 (20% EtOAc/$C_6H_6$); $[\alpha]^{25}_D$−428 (c0.865, $CH_2Cl_2$); IR (neat) $v_{max}$ 3316, 2956, 2932, 2876, 1723, 1686, 1504, 1397, 1289, 1182, 1106; $^1$H NMR (500 MHz, $CDCl_3$) $\delta$7.41–7.39 (m, 2 H, Ph), 7.31–7.28 (m, 2 H, Ph), 7.23–7.19 (m, 1 H, Ph), 6.05 (d, J=2.18 Hz, 1 H, C=CHCH), 5.85 (b d, J=9.49 Hz, 1 H, CH(OH)O), 5.74 (b s, 1 H, NHCOO), 5.63 (d, J=1.56 Hz, 1 H, C≡CCHO), 5.53 (b s, 2 H, CH=CH), 4.33–4.28 (m, 2 H, ethylene ketal), 4.25 (b s, 1 H, OH), 4.18–4.15 (m, 1 H, ethylene ketal), 4.07–4.04 (m, 1 H, ethylene ketal), 3.98–3.94 (m, 2 H, COOCH$_2$CH$_2$SPh), 3.15 (b dd, J=5.98, 6.79 Hz, 2 H, COOCH$_2$CH$_2$SPh), 2.41 (d, J=13.44 Hz, 1 H, CHH-eq), 2.26 (d, J=13.40 Hz, 1 H, CHH-ax), 1.02–0.97 (m, 9 H, Si(CH$_2$CH$_3$)$_3$), 0.82–0.69 (m, 6 H, Si(CH$_2$CH$_3$)$_3$); $^{13}$C NMR (125 MHz, CDCl$_3$) $\delta$140.87, 135.00, 130.01, 129.08, 128.34, 126.63, 124.46, 122.92, 118.78, 105.36, 101.38, 99.98, 89.88, 69.66, 66.19, 65.82, 65.22, 64.07, 64.03, 60.62, 60.42, 45.93, 29.71, 14.21, 7.04, 6.08; FAB HRMS (NBA/NaI) m/e 630.1970, (M+Na$^+$) calcd for $C_{32}H_{37}NO_7SSi$:630.1958.

Compound 33:A solution of lactol 32 (14.4 mg, 23.6 μmol) in MeOH (1 mL) was treated at 0° C. with NaBH$_4$ (34 mg, 0.9 mmol) and the mixture was stirred for 1 h. A second portion of NaBH$_4$ (15 mg, 0.4 mmol) was added to the reaction mixture and stirring was continued for 1 h at 0° C. Acetic acid (200 μL) and water (30 μL) were added and the mixture was stirred for 5 min at 0° C. Solvents were evaporated under vacuum and the reaction mixture was treated further with methanol (200 μL) and water (60 μL) in THF (1 mL) and stirred at room temperature for 15 min. The reaction mixture was poured into brine (5 mL) and extracted with EtOAc (5×10 mL). The organic extracts were dried (Na$_2$SO$_4$), concentrated, and purified by preparative TLC (Et$_2$O) to yield labile diol 33 (9.5 mg, 66%):pale yellow oil; $R_f$= 0.56 (Et$_2$O), 0.10 (70% Et$_2$O in petroleum ether); $[\alpha]^{25}_D$−234 (c0.14, CH$_2$Cl$_2$); IR (neat) $v_{max}$ 3393, 3055, 2955, 2928, 2876, 1716, 1489, 1413, 1319, 1227, 1152 cm$^{-1}$; $^1$HNMR (500 MHz, CDCl$_3$) $\delta$7.41–7.33 (m, 2 H, Ph), 7.32–7.27 (m, 2 H, Ph), 7.26–7.22 (m, 1 H, Ph), 6.38 (b s, 1 H, NHCOO), 6.32 (dd, J=6.18, 7.42 Hz, 1 H, C=CHCH$_2$), 5.88 (d, J=9.44 Hz, 1 H, CH=CHC≡CCH), 5.82 (dd, J= 1.29, 9.45 Hz, 1 H, CH=CHC≡CCH), 5.68 (b s, 1 H, CHOH), 4.53 (b s, 1 H, OH), 4.33–4.22 (m, 4 H, ethylene ketal & CH$_2$OH), 3.99–3.87 (m, 4 H, ethylene ketal & COOCH$_2$CH$_2$OH), 3.19 (b s, 1 H, OH), 3.17 (dd, J= 6.59, 6.64 Hz, 2 H, CH$_2$SPh), 2.53 (d, J=13.87 Hz, 1 H, CH$_2$-eq), 2.17 (d, J= 13.82 Hz, 1 H, CH$_2$-ax), 1.00 (t, J= 7.90 Hz, 9 H, Si(CH$_2$CH$_3$)$_3$), 0.81–0.67 (m, 6 H, Si(CH$_2$CH$_3$)$_3$); FAB HRMS (NBA/NaI) m/e 632.2120, (M+Na$^+$) calcd for $C_{32}H_{39}NO_7SSi$:632.2114.

Compound 34:This compound was prepared as described for 17:colorless oil; $R_f$= 0.45 (70% Et$_2$O in petroleum ether); $[\alpha]^{25}_D$−154 (c0.075, CH$_2$Cl$_2$); IR (neat) $v_{max}$ 3394, 3059, 2956, 2918, 2877, 2853, 1713, 1674, 1503, 1490, 1454, 1412, 1318, 1274, 1225, 1169, 1116 cm$^{-1}$; $^1$H NMR (500 MHz, CDCl$_3$) $\delta$8.05 (d, J=7.32 Hz, 2 H, Bz), 7.55–7.52 (m, 1 H, Bz), 7.44–7.39 (m, 4 H, Bz & Ph), 7.33–7.30 (m, 2 H, Ph), 7.24–7.21 (m, 1 H, Ph), 6.40 (b s, 1 H, NHCOO), 6.34 (dd, J=5.55, 7.10 Hz, 1 H, C=CHCH$_2$), 5.85 (AB q, J= 9.65 Hz, Δv= 20.92 Hz, 2 H, CH=CH), 5.71 (b s, 1 H, CHOH), 5.28 (b m, 1 H, CHHOBz), 5.10 (b m, 1 H, CHHOBz), 4.30 (b m, 2 H, COOCH$_2$CH$_2$SPh), 4.00–3.90 (m, 4 H, ethylene ketal), 3.62 (b s, 1 H, OH), 3.18 (b m, 2 H, COOCH$_2$CH$_2$SPh), 2.54 (d, J= 13.86 Hz, 1 H, CHH-eq), 2.22 (b d, J= 13.82 Hz, 1 H, CHH-ax), 0.99 (t, J= 7.91 Hz, 9 H, Si(CH$_2$CH$_3$)$_3$), 0.88–0.71 (m, 6 H, Si(CH$_2$CH$_3$)$_3$); $^{13}$C NMR (125 MHz, CDCl$_3$) $\delta$171.03, 166.47, 138.80, 133.74, 132.64, 130.18, 129.67, 129.15, 128.49, 128.19, 126.80, 123.38, 65.47, 64.65, 64.30, 63.57, 32.84, 29.69, 22.69, 7.06, 6.13; FAB HRMS (NBA/NaI) m/e 736.2370, (M+Na$^+$) calcd for $C_{39}H_{43}NO_8SSi$:736.2376.

Compound 35:A solution of sulfide 34 (6.8 mg, 9.5 μμmol) in CH$_2$Cl$_2$ (2 mL) was treated at ambient temperature with mCPBA (8 mg, 46 μmol) and the mixture was stirred for 1.5 h. The reaction mixture was purified directly on a preparative TLC plate (Et$_2$O) to give sulfone 35 (7.1 mg, 100%):colorless oil; $R_f$=0.33 (Et$_2$O); $[\alpha]^{25}_D$−211 (c0.36, CH$_2$Cl$_2$); IR (neat) $v_{max}$ 3480, 3397, 3062, 2955, 2925, 2876, 2853, 1715, 1500, 1451, 1412, 1318, 1273, 1225, 1147, 1116 cm$^{-1}$; $^1$HNMR (500 MHz, CDCl$_3$) $\delta$8.06–8.04 (m, 2 H, Ar), 7.95 (b d, J= 7.45 Hz, 2 H, Ar), 7.70–7.67 (b m, 1 H, Ar), 7.62–7.59 (b m, 2 H, Ar), 7.54 (bt, J= 7.38 Hz, 1 H, Ar), 7.43 (bt, J= 7.69 Hz, 2 H, Ar), 6.34 (b m, 2 H, C=CHCH$_2$ & NHCOO), 5.89 (d, J= 9.44 Hz, 1 H, CH=CHC≡CCH), 5.84 (dd, J= 0.93, 9.48 Hz, 1 H, CH=CHC≡CCH), 5.60 (b s, 1 H, CHOH), 5.26 (b m, 1 H, CHHOBz), 5.09 (b m, CHHOBz), 4.47 (b m, 2 H, COOCH$_2$CH$_2$SO$_2$Ph), 4.05 (b s, 1 H, OH), 3.99–3.93 (m, 4 H, ehtylene ketal), 3.48 (b s, 2 H, COOCH$_2$CH$_2$SO$_2$Ph), 2.53 (d, J= 13.79 Hz, 1 H, CHH-eq), 2.21 (b d, J= 13.23 Hz, 1 H, CHH-ax), 0.99 (t, J= 7.90 Hz, 9 H, Si(CH$_2$CH$_3$)$_3$), 0.81–0.70 (m, 6 H, Si(CH$_2$CH$_3$)$_3$); FAB HRMS (NBA/NaI) m/e 768.2270, (M+Na$^+$) calcd for $C_{39}H_{43}NO_{10}SSi$:768.2275.

Compound 1:A solution of the monobenzoate 17 (16.0 mg, 27.1 μmol) in THF (1.4 mL) and H$_2$O (4 drops) was treated with TsOH.H$_2$O (30 mg, 0.15 mmol) and the mixture was stirred at ambient temperature for 36 h. The reaction mixture was diluted with CH$_2$Cl$_2$, passed through a short column of Na$_2$SO$_4$ and purified by preparative TLC (80% Et$_2$O in petroleum ether) to give enone 1 (8.0 mg, 68%):colorless syrup; $R_f$ = 0.43 (80% Et$_2$O in petroleum ether); $[\alpha]^{25}_D$−580 (c0.43, CH$_2$C$_2$); IR (neat) $v_{max}$ 3364, 2956, 1714, 1680, 1601, 1503, 1451, 1315, 1274, 1178, 1118 cm$^{-1}$; $^1$HNMR (500 MHz, CDCl$_3$) $\delta$8.04–8.02 (m, 2 H, Bz), 7.56–7.53 (m, 1 H, Bz), 7.43–7.40 (m, 2 H, Bz), 6.94 (b s, 1 H, NHCOOCH$_3$), 6.43 (dd, J= 4.18, 8.09 Hz, 1 H, C=CHCH$_2$), 6.01 (b s, 1 H, CHOH), 5.90 (dd, J= 1.27, 9.48 Hz, 1 H, CH=CHC≡CCH), 5.86 (d, J= 9.48 Hz, 1 Hz, CH=CHC≡CCH), 5.34 (dd, J= 4.21, 14.31 Hz, 1 H, CHHOBz), 5.10 (dd, J= 8.11, 14.29 Hz, 1 H, CHHOBz), 3.78 (s, 3 H, NHCOOCH$_3$), 3.28 (b s, 1 H, OH), 3.22 (d, J= 16.98 Hz, 1 H, CHH-eq), 2.80 (d, J= 16.97 Hz, 1 H, CHH-ax), 1.85 (b s, 1 H, OH); $^{13}$C NMR (125 MHz, CDCl$_3$) $\delta$191.22, 166.59, 154.70, 137.01, 133.02, 130.02, 129.99, 129.71, 128.33, 125.59, 124.38, 123.81, 100.05, 99.70, 87.79, 84.81, 72.33, 64.47, 64.34, 53.50, 51.95; FAB HRMS (NBA/CsI) m/e 566.0199, (M+Cs$^+$) calcd for $C_{24}H_{19}NO_7$:566.0216.

Compounds 2–5, 7, 9, 10, and 12–15. These compounds were prepared from the Corresponding fully protected intermediates by similar procedures as described above. They exhibit the following physical data.

2:Colorless foam; $R_f$=0.52 (80% Et$_2$O in petroleum ether); $[\alpha]^{25}_D$−206 (c0.655, CH$_2$Cl$_2$); IR (neat) $v_{max}$ 3359, 2923, 2851, 1722, 1722, 1687, 1601, 1504, 1451, 1270 cm$^{-1}$; $^1$H NMR (500 MHz, CD$_3$OD) δ7.94–7.92 (m, 2 H, Bz), 7.74–7.72 (m, 2 H, Bz), 7.46–7.42 (m, 2 H, Bz), 7.34–7.23 (m, 4 H, Bz), 7.00 (d, J= 1.73 Hz, 1 H, C≡CCHOBz), 6.36 (dd, J= 5.26, 7.73 Hz, 1 H, C=CHCH$_2$), 5.98 (d, J= 9.54 Hz, 1 H, CH=CHC=CCH), 5.80 (dd, J= 1.72, 9.52 Hz, 1 H, CH=CHC≡CCH), 4.86 (d, J= 5.25, 13.48 Hz, 1 H, CHHOBz), 4.67 (dd, J= 7.77, 13.50 Hz, 1 H, CHHOBz), 3.59 (s, 3 H, NHCOOCH$_3$), 2.99 (d, J= 17.09 Hz, 1 H, CHH-eq), 2.57 (d, J= 17.10 Hz, 1 H, CHH-ax); $^{13}$C NMR (125 MHz, CD$_3$OD) δ134.94, 134.27, 130.87, 130.55, 129.93, 129.52, 127.01, 125.29, 123.55, 84.13, 65.92, 65.04, 55.25, 53.45; FAB HRMS (NBA/CsI) m/e 670.0478 M+Cs$^+$ calcd for C$_{31}$H$_{23}$NO$_8$ 670.0478.

3:White solid; R$_f$=0.14 (30% EtOAc in petroleum ether); [α]$^{25}_D$–198 (c0.15, CH$_2$Cl$_2$); IR (neat) ν$_{max}$ 3353, 2921, 2852, 1737, 1715, 1683, 1589, 1518, 1496, 1456, 1345, 1271, 1231, 1205, 1115 cm$^{-1}$; $^1$H NMR (500 MHz, C$_6$D$_6$) δ8.17–8.16 (m, 2 H, Ar), 8.15–8.15 (m, 2 H, Ar), 7.76 (s, 1 H, NHCOOCH$_3$), 7.16–7.13 (m, 1 H, Ar), 7.09–7.06 (m, 2 H, Ar), 6.79 (b s, 1 H, CHOCO), 6.75–6.73 (m, 2 H, Ar), 6.50 (dd, J=3.43, 8.61 Hz, 1 H, C=CHCH$_2$), 5.59 (dd, J=3.45, 14.20 Hz, 1 H, CHHOBz), 5.33–5.32 (m, 2 H, CH=CH), 5.31 (dd, J= 8.58, 14.24 Hz, 1 H, CHHOBz), 3.19 (s, 3 H, NHCOOCH$_3$), 3.10 (d, J= 16.86 Hz, 1 H, CH$_2$-eq), 2.62 (dt, J= 7.19, 16.50 Hz, 1 H, CH$_2$), 2.45 (d, J= 16.86 Hz, 1 H, CH$_2$-ax), 2.42–2.34 (m, 3 H, CH$_2$), 2.06 (b s, 1 H, OH), 1.97 (dq, J= 2.10, 7.31 Hz, 2 H, CH$_2$); $^{13}$C NMR (125 MHz, C$_6$D$_6$) δ190.19, 171.26, 170.00, 166.57, 155.33, 153.85, 137.36, 133.20, 129.89, 125.54, 124.99, 124.75, 124.15, 122.28, 100.80, 98.19, 87.77, 84.49, 72.19, 65.81, 64.75, 53.27, 52.85, 52.70, 32.95, 30.41, 30.18, 20.02; FAB HRMS (NBA/CsI) m/e 801.0685, (M+Cs$^+$) calcd for C$_{35}$H$_{28}$N$_2$O$_{12}$:801.0697.

4:Colorless oil; R$_f$= 0.36 (2% MeOH in Et$_2$O); [α]$^{25}_D$– 353 (c0.910, CH$_2$Cl$_2$); IR (neat) ν$_{max}$ 3354, 3062, 2956, 1714, 1684, 1504, 1451, 1273, 1244 cm$^{-1}$; $^1$H NMR (500 MHz, CDCl$_3$) δ8.05–8.04 (m, 2 H, Bz), 7.59–7.55 (m, 1 H, Bz), 7.46–7.43 (m, 2 H, Bz), 6.96 (b s, 1 H, NHCOOMe), 6.75 (d, J= 1.46 Hz, 1 H, CHOCOCH$_2$), 6.48 (dd, J= 3.70, 8.61 Hz, 1 H, C=CHCH$_2$), 5.93 (d, J= 9.49 Hz, 1 H, CH=CHC≡CCH), 5.89 (dd, J= 1.53, 9.48 Hz, 1 H, CH=CHC≡CCH), 5.28 (dd, J= 3.70, 14.01 Hz, 1 H, CHHOBz), 4.99 (dd, J= 8.62, 14.01 Hz, 1 H, CHHOBz), 3.76 (s, 3 H, NHCOOCH$_3$), 3.26 (d, J= 16.96 Hz, 1 H, CHH-eq), 2.82 (d, J= 16.96 Hz, 1 H, CHH-ax), 2.72–2.59 (m, 2 H, CH$_2$COOH), 2.50–2.47 (m, 2 H, CHOCOCH$_2$), 2.09–2.01 (m, 2 H, CH$_2$CH$_2$CH$_2$); $^{13}$C NMR (125 MHz, CDCl$_3$) δ191.19, 178.50, 177.96, 171.55, 166.61, 154.04, 137.00, 133.21, 131.30, 129.69, 128.44, 128.34, 125.51, 124.78, 124.18, 99.75, 96.82, 87.60, 84.37, 72.21, 65.25, 64.14, 53.52, 52.71, 32.89, 32.55, 29.71, 19.74, 19.59; FAB HRMS (NBA/NaI) m/e 570.1360, (M+ Na$^+$) calcd for C$_{29}$H$_{25}$NO$_{10}$:570.1376.

7:Colorless solid; R$_f$= 0.08 (20% EtOAc in benzene); [α]$^{25}_D$–670 (c0.23, CH$_2$Cl$_2$); IR (neat) ν$_{max}$ 3358, 3059, 2925, 2854, 1715, 1675, 1505, 1450, 1316, 1242 cm$^{-1}$; $^1$H NMR (500 MHz, CD$_3$OD) δ6.01 (dd, J=7.20, 8.57 Hz, C=CHCH$_2$), 5.86 (d, J= 9.48 Hz, 1 H, CH=CHC≡CCH), 5.77 (dd, J= 1.75, 9.49 Hz, 1 H, CH=CHC≡CCH), 5.71 (d, J= 1.68 Hz, 1 H, CHOH), 3.73 (dd, J= 8.72, 14.04 Hz, 1 H, CHHSCOCH$_3$), 3.59 (dd, J= 7.14, 14.05 Hz, 1 H, CHHSCOCH$_3$), 3.53 (s, 3 H, NHCOOCH$_3$), 2.84 (d, J= 16.98 Hz, 1 H, CHH-eq), 2.39 (d, J= 16.97 Hz, 1 H, CHH-ax), 2.18 (s, 3 H, SCOCH$_3$); $^{13}$C NMR (125 MHz, CD$_3$OD) δ197.42, 138.54, 127.11, 125.53, 123.99, 101.75, 101.61, 87.69, 83.81, 72.62, 64.08, 55.16, 53.17, 31.60, 30.27; FAB HRMS (NBA/CsI) m/e 519.9816, (M+ Cs$^+$) calcd for C$_{19}$H$_{17}$NO$_6$S:519.9831.

9:White foam; R$_f$=0.11 (70% Et$_2$O in petroleum ether); [α]$^{25}_D$–900 (c0.065, CH$_2$Cl$_2$); IR (neat) ν$_{max}$ 3349, 2922, 1708, 1674, 1508, 1313, 1242 cm$^{-1}$; $^1$H NMR (500 MHz, CDCl$_3$) δ6.90 (b s, 1 H, NHCOOCH$_3$), 6.39 (dd, J= 6.33, 9.52 Hz, 1 H, C=CHCH$_2$), 5.99 (b d, J= 7.40 Hz, 1 H, CHOH), 5.90–5.89 (m, 2 H, CH=CH), 3.89 (dd, J= 9.54, 13.94 Hz, 1 H, CHHSSCH$_3$), 3.78 (s, 3 H, NHCOOCH$_3$), 3.66 (dd, J= 6.28, 13.95 Hz, 1 H, CHHSSCH$_3$), 3.21 (d, J= 16.88 Hz, 1 H, CHH-eq), 3.16 (b d, J= 7.79 Hz, 1 H, OH), 2.83 (d, J= 16.82 Hz, 1 H, CHH-ax), 2.77 (b s, 1 H, OH), 2.37 (s, 3 H, SSCH$_3$); $^{13}$C NMR (125 MHz, CDCl$_3$) δ191.29, 154.40, 137.07, 130.27, 126.99, 124.20, 123.74, 100.03, 99.90, 87.54, 72.54, 64.31, 53.31, 52.84, 37.25, 29.59, 23.00, 11.45; FAB HRMS (NBA/CsI) m/e 523.9591, (M+Cs$^+$) calcd for C$_{18}$H$_{17}$NO$_5$S$_2$:523.9602.

10:White amorphous solid; R$_f$=0.09 (70% Et$_2$O in petroleum ether); [α]$^{25}_D$–590 (c0.17, CH$_2$Cl$_2$); IR (neat) ν$_{max}$ 3334, 2921, 2852, 1715, 1674, 1577, 1501, 1448, 1417, 1314, 1238 cm$^{-1}$; $^1$H NMR (500 MHz, CDCl$_3$) δ8.44–8.43 (m, 1 H, Pyr), 7.64–7.60 (m, 2 H, Pyr), 7.10–7.07 (m, 1 H, Pyr), 6.83 (b s, 1 H, NHCOOCH$_3$), 6.38 (dd, J= 7.85, 8.31 Hz, 1 H, C=CHCH$_2$), 6.01 (b s, 1 H, CHOH), 5.89 (dd, J= 1.20, 9.44 Hz, 1 H, CH=CHC≡CCH), 5.86 (d, J= 9.45 Hz, 1 H, CH=CHC≡CCH), 3.99 (dd, J= 8.55, 13.21 Hz, 1 H, CHHSSPyr), 3.82 (dd, J= 7.58, 13.19 Hz, 1 H, CHHSSPyr), 3.77 (b d, J= 3.02 Hz, 1 H, CHOH), 3.10 (d, J= 16.79 Hz, 1 H, CHH-eq), 2.97 (b s, 1 H, OH), 2.56 (d, J= 16.83 Hz, 1 H, CHH-ax); $^{13}$C NMR (125 MHz, CDCl$_3$) δ191.13, 159.86, 154.33, 149.51, 138.14, 137.07, 130.22, 125.29, 124.26, 123.78, 121.02, 120.90, 100.35, 99.91, 87.55, 84.51, 72.57, 64.48, 53.31, 52.52, 38.28; FAB HRMS (NBA) m/e 442.0660, (M+H$^+$) calcd for C$_{21}$H$_{17}$N$_2$O$_5$S$_2$:442.0657.

12:White amorphous solid; R$_f$=0.21 (80% Et$_2$O in petroleum ether); [α]$^{25}_D$–600 (c0.30, CH$_2$Cl$_2$); IR (neat) ν$_{max}$ 3357, 1718, 1677, 1509, 1438, 1369, 1236 cm$^{-1}$; $^1$H NMR (500 MHz, CD$_3$OD) δ6.12 (dd, J= 3.98, 8.70 Hz, 1 H, C=CHCH$_2$), 5.86 (d, J= 9.50 Hz, 1 H, CH=CHC≡CCH), 5.77 (dd, J= 1.78, 9.50 Hz, 1 H, CH=CHC≡CCH), 5.70 (d, J= 1.68 Hz, 1 H, CHOH), 4.74 (dd, J= 3.97, 13.85 Hz, 1 H, CHHOAc), 4.60 (dd, J= 8.73, 13.85 Hz, 1 H, CHHOAc), 3.54 (b s, 3 H, NHCOOCH$_3$), 2.88 (d, J= 17.00 Hz, 1 H, CHH-eq), 2.46 (d, J= 17.01 Hz, 1 H, CHH-ax), 1.91 (s, 3 H, COCH$_3$); $^{13}$C NMR (125 MHz, CD$_3$OD) δ193.87, 172.78, 139.18, 126.09, 125.50, 124.06, 101.43, 87.71, 83.96, 72.58, 65.49, 63.94, 54.86, 53.19, 20.83; FAB HRMS (NBA/CsI) m/e 504.0050, (M+ Cs$^+$) calcd for C$_{19}$H$_{17}$NO$_7$:504.0056.

13:White powder; R$_f$=0.12 (40% EtOAc in benzene); [α]$^{25}_D$–260 (c0.11, CH$_2$Cl$_2$); IR (neat) ν$_{max}$ 3311, 2923, 2852, 1739, 1676, 1499, 1449, 1259 cm$^{-1}$; $^1$H NMR (500 MHz, CDCl$_3$) δ7.94–7.92 (m, 2 H, SO$_2$Ph), 7.68–7.67 (m, 1 H, SO$_2$Ph), 7.61–7.58 (m, 2 H, SO$_2$Ph), 6.97 (b s, 1 H, NHCOOCH$_3$), 6.25 (dd, J= 4.33, 7.89 Hz, 1 H, C=CHCH$_2$), 5.96 (b d, J= 5.32 Hz, 1 H, CHOH), 5.91 (dd, J= 1.24, 10.71 Hz, 1 H, CH=CHC≡CCH), 5.88 (d, J= 9.48 Hz, CH=CHC≡CCH), 5.02 (dd, J= 4.31, 14.03 Hz, 1 H, CHHOCO), 4.91 (dd, J= 7.92, 14.04 Hz, 1 H, CHHOCO), 4.51–4.42 (m, 2 H, OCOCH$_2$CH$_2$SO$_2$Ph), 3.78 (s, 3 H, NHCOOCH$_3$), 3.52–3.48 (m, 3 H, OCOCH$_2$CH$_2$SO$_2$Ph+OH), 3.20 (d, J= 16.97 Hz, 1 H, CHH-eq), 3.04 (b s, 1 H, OH), 2.76 (d, J= 16.97 Hz, 1 H, CHH-ax); $^{13}$C NMR (125 MHz, CDCl$_3$) δ190.82, 154.55, 154.09, 138.83, 137.51, 134.03, 129.40, 129.36, 128.01, 124.34, 124.18, 123.68, 99.71, 99.35, 87.77, 84.91, 72.18, 67.20, 64.29, 54.7.9, 53.40, 51.65, 31.80, 29.58, 29.54; FAB HRMS (NBA/CsI) m/e 674.0106, (M+Cs$^+$) calcd for C$_{26}$H$_{23}$NO$_{10}$S:674.0097.

14: Colorless oil; $R_f$= 0.23 (EtOAc); $[\alpha]^{25}_D$ −210 (c0.08, CH$_2$Cl$_2$); IR (neat) $v_{max}$ 3313, 2921, 2852, 1712, 1551, 1464, 1243 cm$^{-1}$; $^1$H NMR (500 MHz, CDCl$_3$) δ7.07 (b s, 1 H, NHCOOCH$_3$), 6.76 (dd, J= 8.83, 9.45 Hz, 1 H, C=CHCH$_2$), 6.08 (b m, 1 H, NHCOCH$_3$), 5.94 (d, J= 4.18 Hz, 1 H, CHOH), 5.85 (d, J= 9.59 Hz, 1 H, CH=CHC≡CH), 5.82 (dd, J= 1.02, 9.47 Hz, 1 H, CH=CHC≡CH), 4.48–4.41 (m, 1 H, CHHNHCOCH$_3$), 4.40–4.37 (m, 1 H, CHHNHCOCH$_3$), 3.78 (s, 3 H, NHCOOCH$_3$), 3.74 (b d, J= 4.04 Hz, 1 H, CHOH), 3.17 (d, J= 17.42 Hz, 1 H, CHH-eq), 2.94 (d, J= 17.39 Hz, 1 H, CHH-ax), 2.00 (s, 3 H, NHCOCH$_3$); $^{13}$C NMR (125 MHz, CDCl$_3$) δ191.47, 124.47, 123.77, 123.28, 66.30, 53.54, 49.98, 36.17, 29.71, 29.67, 23.16, 14.21; FAB HRMS (NBA/CsI) m/e 503.0235, (M+Cs$^+$) calcd for C$_{19}$H$_{18}$N$_2$O$_6$:503.0219.

15: Coldess oil; $R_f$=0.53 (Et$_2$O); $[\alpha]^{25}_D$ −167 (c0.11, CH$_2$Cl$_2$); IR (neat) $v_{max}$ 3367, 3061, 2924, 2853, 1714, 1680, 1601, 1504, 1450, 1396, 1274, 1142 cm$^{-1}$; $^1$H NMR (500 MHz, CDCl$_3$) δ7.98–7.97 (m, 2 H, Ar), 7.89–7.85 (m, 2 H, Ar), 7.64–7.61 (m, 1 H, Ar), 7.57–7.53 (m, 2 H, Ar), 7.51–7.48 (m, 1 H, Ar), 7.39–7.35 (m, 2 H, Ar), 6.6 (b s, 1 H, NHCOO), 6.36 (dd, J= 4.35, 7.97 Hz, 1 H, C=CHCH$_2$), 5.86 (dd, J= 1.22, 9.50 Hz, 1 H, CH=C≡CCH), 5.83 (d, J= 9.46 Hz, 1 H, CH=CHC≡CH), 5.21 (dd, J= 4.02, 14.22 Hz, 1 H, CHHOBz), 5.00 (dd, J= 9.34, 14.05 Hz, 1 H, CHHOBz), 4.44 (b m, 2 H, COOCH$_2$CH$_2$SO$_2$Ph), 3.49–3.40 (m, 3 H, CH$_2$SO$_2$Ph & OH), 3.12 (d, J= 16.92 Hz, 1 H, CHH-eq), 2.78 (b s, 1 H, OH), 2.71 (d, J= 16.91 Hz, 1 H, CHH-ax); $^{13}$C NMR (125 MHz, CDCl$_3$) δ193.41, 166.55, 153.06, 136.79, 134.22, 133.09, 129.98, 129.69, 129.52, 129.36, 128.37, 128.10, 125.84, 124.35, 123.94, 99.56, 72.34, 65.86, 64.26, 59.54, 55.10, 31.92, 29.70, 29.36, 22.69, 15.27, 14.12; FAB HRMS (NBA/NaI) m/e 610.1153, (M+Na$^+$) calcd for C$_{31}$H$_{26}$NO$_9$S:610.1148.

What is claimed is:

1. A calicheamicin mimic represented by the following structure:

wherein R is selected from the group consisting of:

R = CO(CH$_2$)$_3$CO$_2$H and

2. A calicheamicin mimic represented by the following structure:

3. A calicheamicin mimic represented by the following structure:

wherein R is represented by the following structure:

* * * * *